United States Patent [19]

Hatzakis, Jr. et al.

[11] Patent Number: 5,837,978
[45] Date of Patent: Nov. 17, 1998

[54] RADIATION CONTROL SYSTEM

[75] Inventors: Michael Hatzakis, Jr., Chappaqua; David Andrew Lewis, Carmel, both of N.Y.; Jane Margaret Shaw, Ridgefield, Conn.

[73] Assignee: International Business Machines Corporation, Armonk, N.Y.

[21] Appl. No.: 770,213

[22] Filed: Dec. 19, 1996

Related U.S. Application Data

[63] Continuation of Ser. No. 155,071, Nov. 18, 1993, abandoned, which is a continuation of Ser. No. 782,841, Oct. 29, 1991, abandoned, which is a continuation-in-part of Ser. No. 551,716, Jul. 11, 1990, Pat. No. 5,241,040.

[51] Int. Cl.$^6$ .................................................... H05B 6/66
[52] U.S. Cl. ........................................ 219/702; 219/705
[58] Field of Search .................................. 219/702–712, 219/719, 720

[56] References Cited

U.S. PATENT DOCUMENTS

| | | | |
|---|---|---|---|
| 2,636,975 | 4/1953 | Baker et al. | 219/10.55 A |
| 4,324,965 | 4/1982 | Naumann et al. | 219/10.55 F |
| 4,667,076 | 5/1987 | Amada | 219/10.55 M |
| 4,728,910 | 3/1988 | Owens | 219/10.55 A |
| 4,760,228 | 7/1988 | Kudo | 219/10.55 A |
| 5,069,928 | 12/1991 | Echizen et al. | 219/10.55 A |
| 5,134,262 | 7/1992 | Lee | 219/10.55 B |
| 5,153,406 | 10/1992 | Smith | 219/10.55 A |

OTHER PUBLICATIONS

Robert Pennisi, "Simulation and Analysis of In–Line Thermal and Microwave Curing of Tab Encapsulants", 1988 IEEE, pp. 45–48, CH2629–4/88/0000–0045.

Robert Pennisi, "Simulation and Analysis of Thermal and Microwave Curing of Tab Encapsulants", 1987 IEEE, pp. 40–45, CH2483–6/88/0000–0040.

Jinder Jow et al., "Microwave Processing and Diagnosis of Chemically Reacting Materials in Single–Mode Cavity Applicator" 1987 IEEE, pp. 1435–1443, 0018–9480/87/1200–1435.

*Primary Examiner*—Tu B. Hoang
*Attorney, Agent, or Firm*—Daniel P. Morris

[57] ABSTRACT

A control system for a blind microwave radiation tool a workpiece is described. The controlled system automatically tunes the cavity containing the workpiece. The control system automatically controls the temperature of the workpiece according to a predetermined temperature versus time schedule. Control system automatically determines when the workpiece has reached a particular predetermined physical condition. To achieve these results the control system automatically monitors applied power, reflected power or current temperature and automatically controls the microwave antennae location and the cavity short location in order to maintain the cavity in resonance and to determine when to exit without operator intervention. Control system can run on a small computer and is useful for automatically curing polyamic acid to polyimide to a predetermined percent cure automatically without operator intervention.

22 Claims, 12 Drawing Sheets

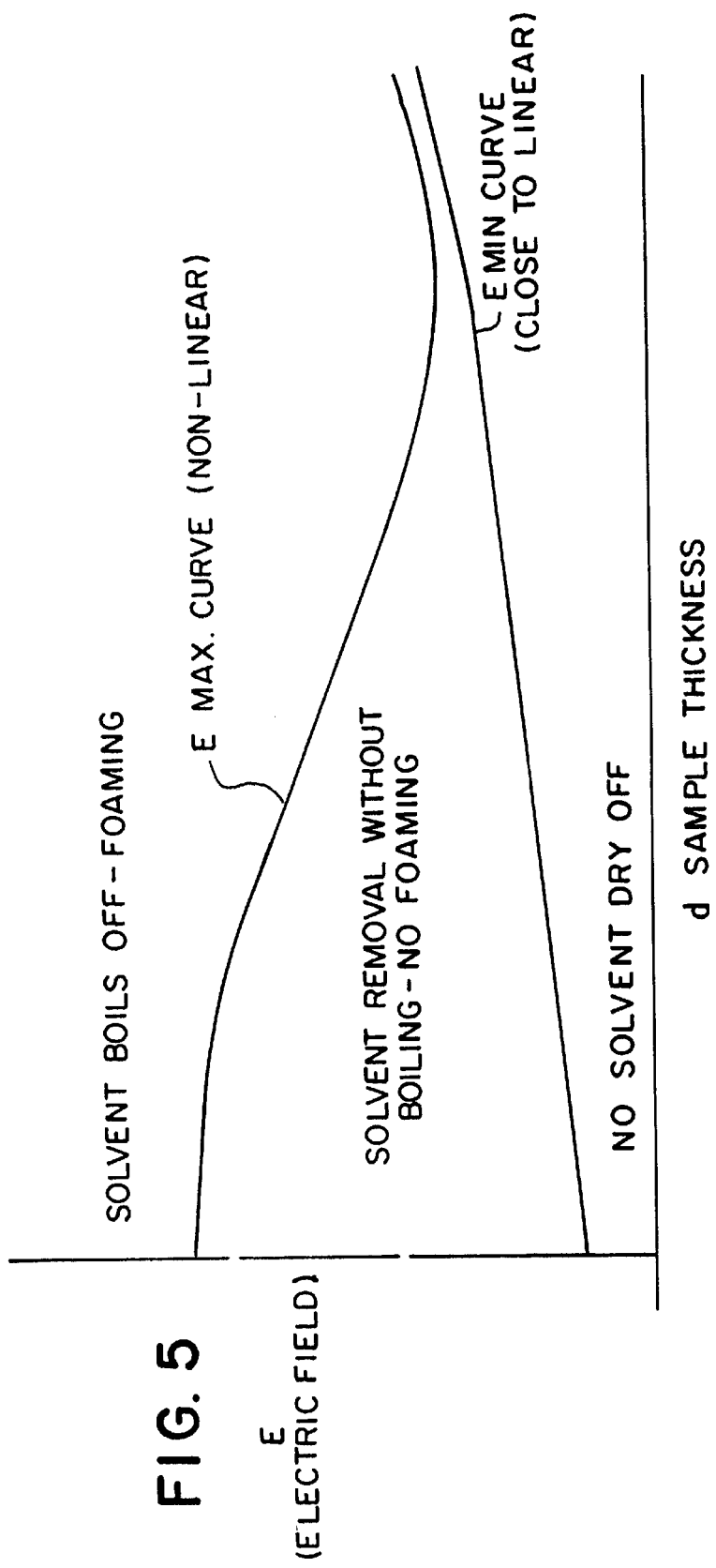

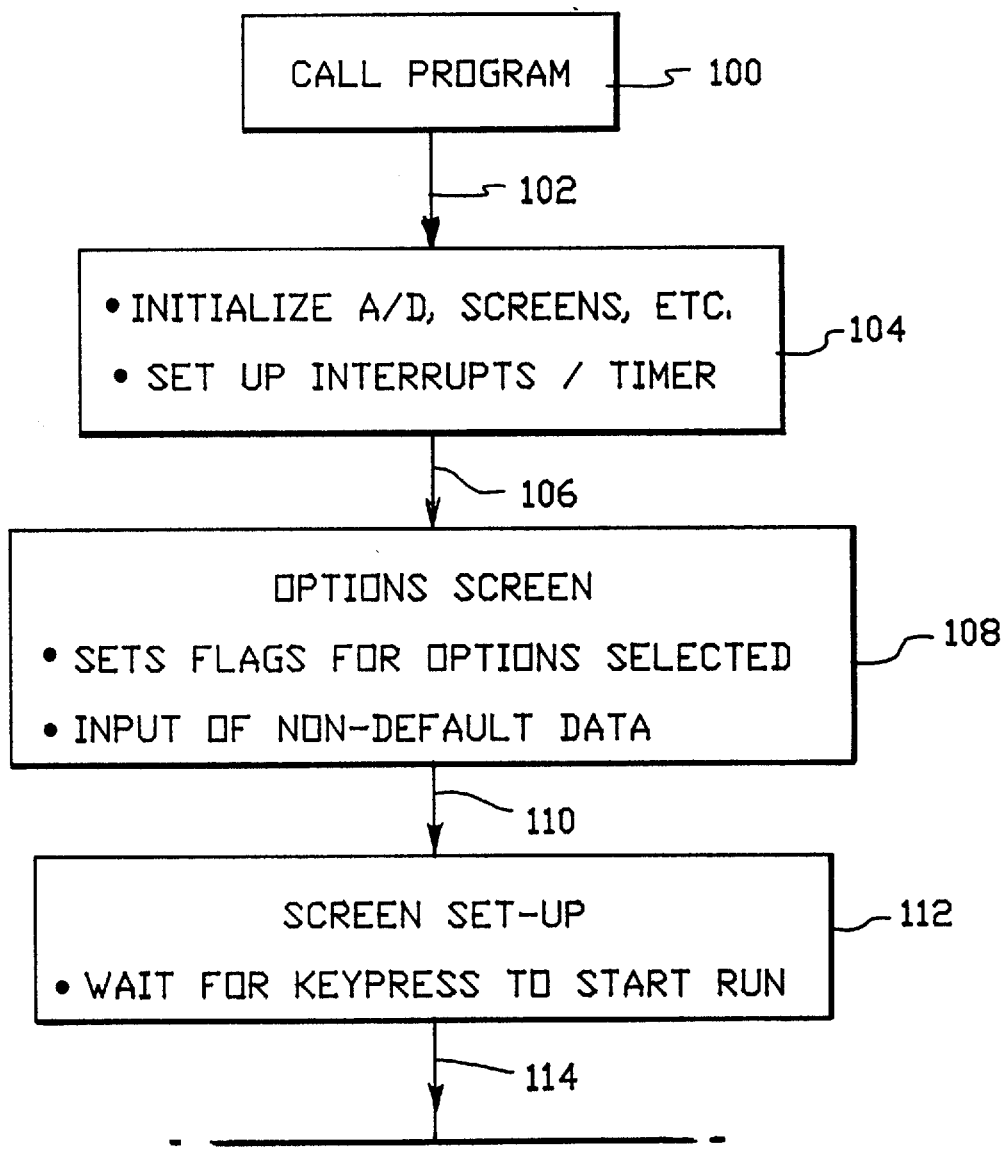

RADIATION CONTROL SYSTEM

This is a continuation of application Ser. No. 08/155,071, filed Nov. 18, 1993, abandoned, which is a continuation of application Ser. No. 07/782,841, filed Oct. 29, 1991, as now abandoned Jan. 13, 1994 which is a continuation-in-part of U.S. application Ser. No. 07/551,716 filed Jul. 11, 1990, U.S. Pat No. 5,241,040.

DESCRIPTION

FIELD OF THE INVENTION

This invention relates to methods and systems for automated control of a radiation apparatus useful for the application of microwave radiation to physical processes and chemical reactions such as the preparation of polyimide polymers from polyamic acid precursors dissolved in a solvent in which the solvent is volatilized by microwave radiation followed by imidization of the precursor by microwave radiation. More particularly, the system is a computer control system. More particularly, the invention is directed to automated methods and systems for the application of microwave radiation to the precursor to automatically control the degree and rate or the imidization and to accurately determine the end point of or degree of imidization by an in situ non-destructive testing method without operator intervention.

BACKGROUND

In the fabrication of integrated circuits such as microcircuits, insulating layers are applied over the circuits or utilized in sandwich construction. These layers in some applications comprise polyimide films. The conventional polyimides utilized in this respect are prepared from precursors that contain polyamic acid groups, polyamic ester groups or combinations thereof, the precursors in turn being prepared by the reaction of a dianhydride and diamine or a diester-diacid dichloride and diamine. The precursor that is produced is soluble in common organic solvents and when dissolved, can be applied to various substrates as a coating. After the substrate is coated the solvent is removed, usually by the application of heat to the coated substrate and with continued heating, the precursor is converted into a polyimide film with the evolution of water or alcohol as a product of the imidization reaction. The polyimide film obtained is not readily soluble in conventional solvents, is extremely strong, has excellent high temperature performance and can be made to adhere to most substrates. Because of the outstanding physical properties of polyimide resins, they have been widely used in many coating applications. One of the disadvantages of polyimides in all of the foregoing reactions is the cure time necessary to develop the ultimate mechanical properties which typically in thin film applications can be as high as ten to twelve hours.

As noted, the precursor is converted to the polyimide with the evolution of water or alcohol as a by-product of reaction. This imidization usually begins at about 150° C. whereas temperatures upwards of about 300° C. are required to complete the process which is sometimes referred to as dehydration and temperatures up to 400° C. are required to complete ordering processes for some polyimides.

In curing polyamic acid by this dehydration process to form the polyimide polymer, care must be excerciesd to ensure that even heating is effected throughout the cross-section of polyamic acid being converted, which is not always easy to achieve. For example, when films of polyamic acid are exposed to heat in conventional ovens, the film cures from the outer most surface inwardly and if the curing process proceeds at too high a rate, the outer surface of the film will be (i) cured significantly faster than the center, possibly resulting in void formation, or (ii) result in inferior mechanical properties Such as reduced modulus, enhanced swelling, solvent uptake and CTE (coefficient of thermal expansion The prior art contains general disclosures regarding the use of microwave radiation to convert polyamic acid precursors to polyimides (U.S. Pat. Nos. 4,305,796 and 4,439,381 to Gagliani et al. and U.S. Pat. No. 4,681,654 to Clementi et al.), however, as a practical matter greater than 50% conversion of the precursor to the polyimide has not been obtained.

It is believed that the problems encountered with microwave curing of polyamic acids to polyimides is due in large measure to the microwave device employed. The microwave apparatus conventionally utilized in this regard is similar in operation to a "home microwave" i.e. a large, multimode chamber with one or more magnetrons coupling microwave radiation into the chamber. These systems typically operate at full power which is regulated by turning it on or off, resulting in a form of "pulsed" radiation treatment. This apparatus has the disadvantages of non-uniform microwave fields which vary spatially with the movement and/or curing of the part and difficulty in providing controlled evaporation and curing rates. This can result in non-uniform curing on a small level, which in turn results in enhanced local stress in the film, since these materials shrink on curing. In addition, solvent evaporation is difficult to control resulting in poor film quality and it is difficult in such an arrangement to obtain sufficiently high electric field strengths (power density) to obtain full or substantially full cure of the polyimide. Gagliani et al. (supra) even describe the use of short bursts of microwave radiation in this regard.

Thus the prior art solution to the difficulties encountered with microwave curing was to employ the microwave process only for partial imidization of polyamic acids to polyimides and subsequently heating the product obtained by means other than microwave radiation.

One of the other difficulties encountered in the prior art was that in situ test means were not available to determine the degree of imidization of the polyamic acid to polyimide. The product had to be removed from the imidizing reaction milieu and tested, either by wet analysis to determine the carboxylic acid groups in the product or by other test methods such as FTIR spectroscopy and the like.

These prior art methods employing microwave radiation also did not lend themselves to the precise control of the rate and degree of imidization of polyamic acid to polyimides over a range from partial imidization to substantially complete imidization in such a way as to optimize the mechanical properties of the imidized product.

There has also been no disclosure in the prior art of a method for exposing a polyimide precursor material to microwave radiation when the precursor has been placed on a substrate such as metal containing PC boards or various metal oxides such as alumina with metal wiring and pads and metal over Kapton (trademark) polyimide. It is usually assumed that arcing between the metal pads would result and damage the pads and dielectric material.

In an apparatus of our invention, the work piece is held in a single mode microwave applicator, hereinafter referred to as a cavity, which is held in tune by minimizing the reflected microwave power as the physical properties of the work piece are changed as a result of the application of the radiation. Also, the temperature versus time progress of the workpiece is monitored and controlled according to a predetermined schedule by control of the radiation intensity.

In an apparatus of our invention the temperature versus time progress of a workpiece in a cavity is monitored and controlled according to a predetermined schedule by control of the radiation intensity while at the same time the same cavity is held in tune while at the same time the physical properties of the workpeice change as a result of the application of the radiation; by varying the location of the radiation source and cavity short with respect to the workpiece. The Q of the cavity is monitored and from the temperature—Q history it is determined when the workpiece has achieved a predetermined physical condition and when to stop the application of the radiation. Prior art methods manually control these types of procedures and at best heave only partial automated control. The applicants have invented a complete automated control process.

U.S. Pat. No. 4,324,965 describes a method by which to automate the movement of a triple stub tuner in a waveguide wherein two stubs are moved at different rates simultaneously. In contradistinction, according to the present invention two axes are moved independently at independent speeds and to independent distances which provides a substantial enhancement.

U.S. Pat. No. 4,667,076 describes an apparatus for annealing a silicon wafer having elements to control temperature and gaseous environment. There is no need to tune the chamber since radiation emitting horn is used. There is no teaching or suggestion of end point detection.

U.S. Pat. No. 4,760,228 describes microwave heating of a extradite from an extruder for which there is no built in control elements. Reflected power is minimized by the system design and is not controllable. Temperature is adjusted to a steady state by fixing the microwave power at a predetermined value.

It is an object of the present invention to provide a complete automation system to apply radiation to a workpiece and to automatically determine when to cease exposure to the radiation when the workpiece has reached a predetermined physical condition.

BRIEF DESCRIPTION OF THE DRAWINGS

FIG. 5 comprises a plot of the electric field strength E of microwave radiation employed according to the present invention where the power of such radiation is directly related to the square of E. The electric field E is a value on the Y axis lying between E max and E min for a polyimide precursor dissolved in the solvent and is obtained by establishing where solvent removal is obtained without boiling i.e. no foaming, which is a value between E min, where electric field is too small to result in solvent drying and E max, those values where the solvent boils off causing foaming of the polyamic acid at various thicknesses "d" plotted along the X axis.

SUMMARY OF THE INVENTION

Figure 1:
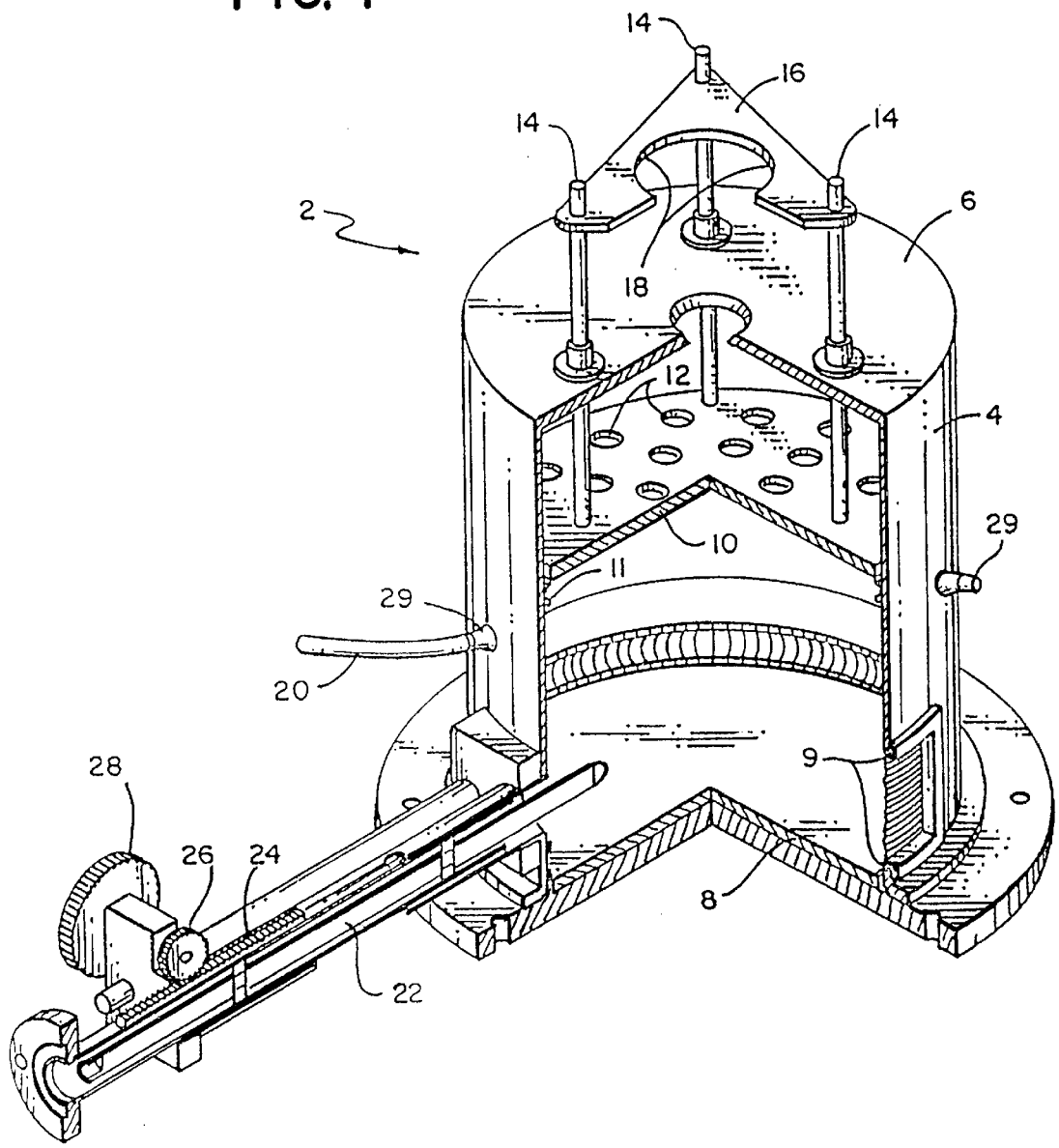
FIG. 1 comprises a three dimensional view of a tuneable microwave cavity processing system according to one embodiment of the invention.

In its broadest aspect, the present invention is a system for maintaining a cavity containing a work piece at resonance in which the physical parameters of the workpiece change on exposure to radiation.

In a more particular aspect, the present invention relates to a system for applying radiation to a workpiece in a cavity. The system has a means for producing a first signal indicative of the Q of the cavity; a means for producing a second signal indicative of the intensity of the radiation applied to the work piece; a means for producing a third signal indicative of the time rate of change of the temperature of the workpiece; and a means responsive to the first, second, third and fourth signals to produce a signal indicative of the value of the intensity of the radiation in the cavity and to maintain the cavity at resonance.

In another more particular aspect of the present invention, the first, second, third and fourth signals are signals in a computer which in response thereto produces a signal indicative of the value of the intensity or the radiation in the cavity and to maintain the cavity at resonance.

These and other objects, features and advantages will be more apparent from the following detailed description, claims and the drawings appended thereto.

DETAILED DESCRIPTION

For convenience the invention will be described primarily for use in curing polyamic acid to polyimide. However, the present invention is not limited to this use. The present invention comprises the application of microwave radiation to physical processes and chemical reactions in a controlled manner so as to obtain products from these processes that are substantially defect free in a minimum amount of time.

The microwave radiation frequency is selected so that it will be absorbed by the sample and the electric field strength E is also selected between minimum (E min) and maximum (E max) values which are empirically measured so that the product obtained when irradiated at an electric field strength E will possess optimum properties. This method is applicable to physical processes such as drying samples e.g. removing solvent from polyimide precursors or water from ceramic materials and/or chemical processes such as the imidization of polyimide precursors and the curing of ceramic materials.

The present invention also comprises applying microwave radiation to such physical processes and chemical reactions in a tuneable microwave cavity so that microwave power is varied over time, based on the quality of cure factor ,"Z" (defined hereafter) in such a way to obtain a substantially defect free product in a minium amount of time. The Z factor or cure fraction refers to the quality of cure or completion of the reaction whether a physical process or a chemical reaction in which the invention is employed.

Microwave radiation is applied to either a physical process or chemical reaction in order to obtain a predetermined value for Z or quality of cure factor which, in a tuneable microwave cavity, is a function of the Q factor (sometimes referred to as the quality factor), and temperature of the system. The Q factor in turn is based on the absorption of the microwave radiation applied to the process and in turn is measured by a comparison of the applied microwave power and reflected microwave power in the system over a range of frequencies or cavity heights and can be related to the dielectric loss factor for the workpiece in the cavity. Typically, the Q factor is calculated from a frequency sweep of the resonant cavity by ratioing the resonant frequency with the width of the resonance at half height. An alternate method is to use a constant frequency and vary the height of the cavity. The value to which we will refer to as the Q factor is determined using the latter approach and in the simplest form, using the width of the tuning dip from resonance to a point with a preselected amount of reflected microwave power, eg. 30% of the forward power. Where reflected microwave power is minimized (which is to say that a maximum amount of microwave power is transmitted into the cavity to be absorbed by the sample being dried or cured and a minimum amount of microwave power is reflected by the system) the system is said to be critically couple, or at resonance, which is the desired state. Since the Q factor varies with temperature and the change of physical state of the system (i.e. the change of the dielectric constant due to chemical and/or physical changes) the Q factor alone will not by itself provide a sufficient basis for obtaining maximum results from the application of microwave radiation to either the chemical reaction or physical process. Accordingly, the Z of the system which is a function of the quality factor Q and the temperature of the system is employed according to the present invention so as to provide an indication of how microwave power is to be varied over time (based on Z) in such a way as to produce a product that has been processed to a precise predetermined degree in a minimum amount of time. Microwave power is therefore varied over time based on Z in such a way to produce a substantially defect free material in a minimum amount of time where this power is applied either in a physical process (e.g. drying or solvent removal) or a chemical process (e.g. polymerization or curing a ceramic material).

The Q factor is determined for the system (which is based on the microwave apparatus, e.g. the cavity, the substrate on which the precursor is mounted, and the and/or polyimide depending on the degree of imidization) combined with sample temperature and indicates when the precursor is substantially completely imidized or any degree of partial imidization is reached. The imidization therefore may be controlled to a reasonably precise predetermined end point and measured without removing the polyimide from the microwave apparatus or employing destructive testing methods for measuring to the degree of imidization to the polyimide.

By employing the method of the invention a thirty fold reduction of the processing time has been obtained.

The invention may be employed in processes for coating integrated circuits such as microcircuits with polyimide films or any other substrate such as a semiconductor substrate, an electrical insulator substrate or any combination thereof, including metal and/or electrical wiring within the insulator substrate.

Utilization of a microwave apparatus that comprises a tuneable microwave resonant cavity that is tuned during the processing to achieve resonance of the system is essential to the practice of one embodiment of the invention.

The present invention in one embodiment comprises a system and apparatus for automated manufacturing of a polyimide by introducing a polyimide precursor containing polyamic acid groups, polyamic ester groups or the equivalents thereof into a microwave apparatus by which microwave radiation may be applied to the precursor. The precursor is the work piece in combination with tile microwave apparatus comprises a working apparatus. The workpiece is then irradiated with the microwave radiation. When the work piece is polyamic acid it is irradiated to convert it to the polyimide. The radiation may also be employed to initially remove solvent from the precursor in such a way as to avoid imperfections in the precursor such as voids, surface irregularities (e.g. pits) and the like. One feature of the microwave apparatus is that it comprises a tuneable microwave resonant cavity means; another feature of the apparatus is it employs a variable power input whereby the power of the microwave radiation during the imidization is adjusted to control the degree and rate of imidization of the precursor.

It has also been discovered according to the present invention that the Q factor of the working apparatus changes as the workpiece physical characteristics change as a result of the irradiation and can be monitored during imidization.

The process cycle can be stopped at any one of several Q factor temperature combinations, depending on the degree of change (imidization) that is to be achieved which in the case of a polyamic acid work piece is from freshly cast precursor in solvent up to substantially complete cure.

Figure 4:
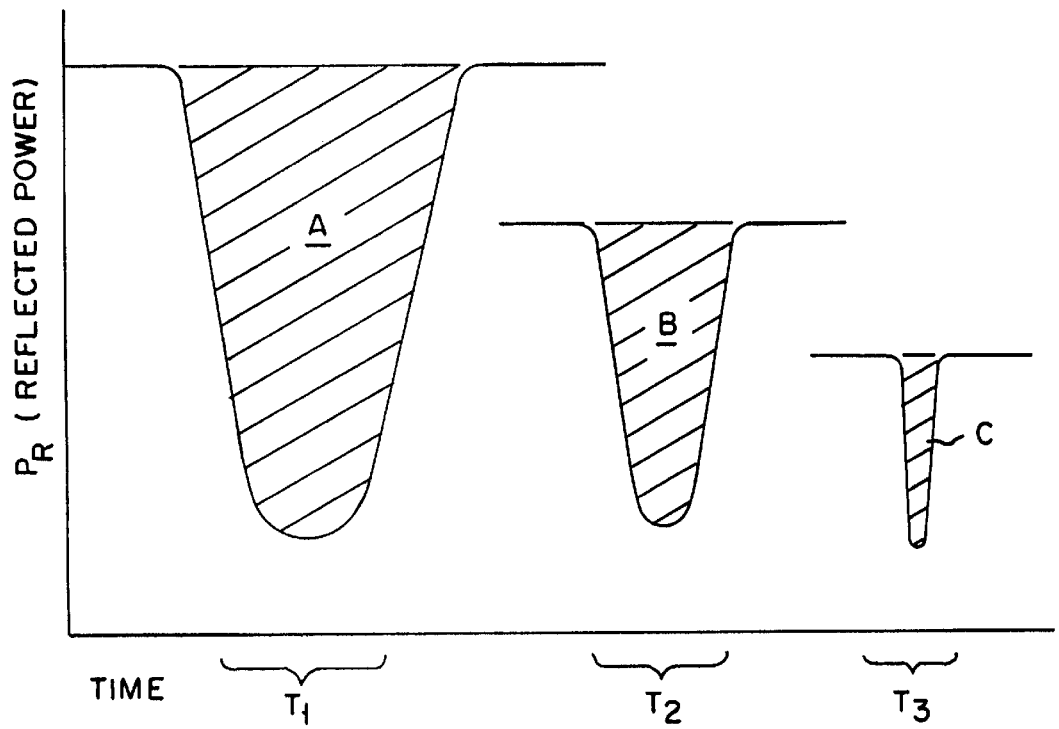
FIG. 4 comprises a plot of the reflected microwave power against the height of the cavity of the apparatus of FIG. 1, wherein the Q factor (i.e. quality factor) for the system is related to the reciprocal of the width at half height of the resonant (lip (for constant frequency input) obtained by monitoring the microwave power reflected from the coupling to the cavity.

The Q factor, as that expression is used throughout this specification, is the quality factor of the microwave cavity with the work piece therein (referred to herein as the working cavity) and is determined from the reciprocal of the width at half height of the resonant dip obtained as shown in FIG. 4 by monitoring the microwave power reflected from the power coupling to the cavity as the cavity height is varied. This is also illustrated in FIG. 4 where reflected power is plotted against height of the cavity.

In FIG. 4, reflected power is plotted along the Y axis and cavity height along the X axis for a single precursor containing polyamic acid (or ester) that is exposed to microwave radiation in such apparatus. Since the precursor absorbs energy relatively strongly in the initial phases of the process, the width of the resonance curve (FIG. 4) will be relatively large giving a lower Q factor. As the imidization proceeds and solvent removed, less microwave power is absorbed by the sample resulting in a reduction in the width of the resonant dip in FIG. 4, thereby corresponding to an increase in Q. Since the absorption of microwave energy is temperature dependent, as governed by (the loss factor) and also the physical state of the film (e.g. glass or rubber) the Q factor will also be temperature dependent.

In each one of the time intervals, T1, T2 and T3 in FIG. 4 the microwave resonance of the tuneable cavity of the apparatus changes because the structure of the polyamic acid changes i.e. the polyamic acid/solvent combination is converted to a combination having mostly polyamic acid, some polyimide formation and some residual solvent to a material which is substantially solvent free and substantially completely polymerized to a polyimide with various degrees of imidization and solvent removal between the two extremes. This causes changes in the resonance of the cavity which is compensated for by tuning the cavity to maximum resonance (critical coupling) which corresponds to minimum reflected power (or zero reflected power). The tuning of the cavity is effected by moving the short 10 of the microwave apparatus upwardly or downwardly during the process and the coupling probe 22 in and out of the cavity.

As an example, power levels P1–P4 are applied( to a polyamic acid precursor dissolved in solvent which is coated on a plate that is positioned on bottom wall 8 in the tuneable cavity 2 of FIG. 1. Power is applied for a period of four time intervals to develop Q values of 8,000, 9,500, 10,000 and 10,500 to initially drive solvent off from the film followed by partial imidization going up through substantially complete imidization. These steps may be summarized in tile following Table 1.

| Power | Q | Temp | |
|-------|--------|---------|---|
| P1 | 8,000 | 130–150 | Begin driving off solvent |
| P2 | 9,500 | 170 | More solvent driven off |
| P3 | 10,000 | 180 | Begin imidization, drive off residual solvent. |
| P4 | 10,500 | 250–350 | Complete imidization |

The Q-factor coupled with the sample temperature provides a "quality of cure" factor "Z" which is a single value that describes the state of cure of the system (as determined by IR and the like) . The analytical relationship between Z, Q and temperature can be determined from a series of measurements of Q, temperature and the degree of conversion of the precursor to the polyimide as determined by FTIR and equivalents thereof. The Z factor therefore is obtained by measuring values of Q at a definite temperature and a definite degree of conversion and is an absolute value that can be measured for any reactants employing any microwave device and any workpiece whose physical characteristics change on exposure to radiation.

The Z factors can then be utilized to specifically indicate the degree of imidization to a polyimide of any subsequent run whether to obtain partial imidization or substantially complete imidization and thereby provides a method for the measurement of the degree of imidization without removing the material from the microwave apparatus. This is a nondestructive testing method for determining in situ the degree of imidization, but is not limited to imidization reactions.

Thus the invention is applicable to any process that absorbs microwave energy. The power of the microwave device is varied over time based on Z in such a way to produce a substantially precise end point of the reaction in a minimum amount of time to obtain a product of the desired quality, e.g. one free of voids and having substantially uniform physical and electrical properties. When microwave energy is applied according to the present invention for the manufacture of polymeric films which can be foamed either because of the entrapment of products of reaction (alcohols and/or water in the case of the conversion of polyamic acid or ester precursors to polyimides) or because the precursor is employed in combination with a solvent, the microwave power is varied over time based on Z in such a way to produce a substantially defect free film in minimum time.

Although the method of the invention has been described with reference to the manufacture of polyimide films it is also applicable to the manufacture of any compounds and the sample or reaction milieu will absorb microwave energy whether for the manufacture of organic or inorganic compounds. For example, the process of the invention may be employed for the manufacture of laminates based on polyesters, epoxies, phenolics, acrylates and the like or the manufacture of such polymeric materials in non-laminate structures. Similarly, ceramic materials may also be dried and/or reacted employing the method of the invention.

The process of the invention can also be employed for removing solvents from substrates not only where the solvent in the precursor is removed by a controlled application of microwave power prior to curing but also for drying other materials such as removing the solvent from a photoresist to a precise level, removing solvent or the liquid reaction medium from the by-products of physical processes or chemical reactions especially those in which solvent removal promotes the growth of crystalline materials and the like.

Although the invention has been described with reference to a tuneable microwave cavity whereby the resonance of the system can be maintained by varying the cavity height or the radiation frequency or the position of the probe 22 in the cavity to match the impedance of the cavity, other systems which do not employ a microwave resonant cavity can also be employed and the process of the inventions utilized.

Maximum properties with this type of apparatus can be obtained by varying the frequency of the microwave radiation, a sweep oscillator system being utilized in this latter respect. For example, a sample not in a cavity is exposed to microwave radiation by one or more microwave antennas similar to radar antennas.

The physical parameters which control the application of microwave energy to obtain maximum results such as imidization of polyamic acid precursors or physical processes involving the removal of solvents or liquids from samples, is both the radiation frequency, (i.e. the radiation must be absorbed by the sample) and the electric field strength. The power of the radiation is related to the square of the electric field strength. A sample, such as a polyimide precursor may be disposed on a surface to form a surface layer of thickness "d." Radiation is applied which is absorbed by the sample e.g. the precursor molecules generating heat at the sites on the molecules where the radiation is absorbed. This heat flows from the points of generation thereby heating the sample. Since a thin film has a large surface area (compared to its volume), much of this heat is lost at the surface preventing the sample from reaching a temperature sufficient to remove the liquid or solvent and to continue with the process such as imidizing the precursor. Therefore, the electric field must reach a minimum value, E min, before solvent or liquid removal and subsequent processing can occur such as imidization. At the same thickness "d," if the electric field exceeds a maximum value, E max, the sample temperature will rise too fast causing the solvent or liquid in the sample to boil generating bubbles which, in the case of imidizing a polyamic acid precursor, will get trapped as the viscosity increases and the solvent is driven off. This results in foaming of the sample. Therefore, for a sample thickness "d" where E max and E min have a functional dependence on "d," as "d" increases, E max decreases because as the sample gets thicker the volatiles generated have a longer distance to travel or diffuse to the surface of the sample where the trapped gas is liberated. The E min curve increases as the sample thickness increases since the volume of the material increases with sample thickness. Power applied is proportional to $E^2$. At a given E, as the thickness increases, the power is absorbed by more material and therefore the temperature does not rise as much. Thus, as thickness increases E min must increase for the solvent to be driven off and for a subsequent imidization period. This is illustrated graphically in FIG. 5. By placing the system under vacuum, the absolute values of E min are reduced, and similarly the absolute values of E min increase if the system is placed under pressure, but the principal remains valid.

After the solvent is driven off, the process proceeds during which there is a minimum E to start imidization and a maximum E beyond which the rate of generating vaporized solvent during imidization will exceed the rate of solvent diffusion out of the sample resulting in defects in the sample such as tie entrapment of vaporized solvent trapped as bubbles or foam or which may cause fractures in the sample.

In conducting the imidization according to the present invention and by employing the apparatus disclosed herein it has been observed that vapor produced during the course of imidization, if not removed from the system may condense on the surface of the polyamic acid and/or polyimide being formed causing irregularities in the surface which ultimately affect the physical properties of the polyimide. In addition, the film quality, void frequency, planarity and the like are affected by solvent condensation on the film during processing.

The vapor in this regard comprises water vapor and/or solvent that may be employed to dissolve the polyimide precursor, the former being present primarily because of the dehydration mechanism by which the imidization of polyamic acid proceeds to the polyimide.

Accordingly, the microwave resonant cavity is provided with means for removing the vapor by using a perforated short 10 or screen in lieu of the perforated short to allow vapor to be removed from the chamber. Ports are strategically located around the periphery of the chamber communicating with the interior thereof which may be connected to vacuum means, pressurized gas or both. The gas may be an inert gas e.g. nitrogen so that an inert atmosphere may the provided around the sample.

It has also been discovered that improved film quality can be obtained if the process is conducted so as to remove the solvent prior to actively converting the precursor into the polyimide. This is obtained by adjusting the initial power of the microwave apparatus during the process so that the temperature of the precursor is sufficiently raised to drive off the solvent as vapor at a controlled rate prior to completion of the imidization so that the precursor and the polymer that is formed is substantially free of voids and solvent. The power of the apparatus is also adjusted to substantially prevent foaming and bubbling of the film while the vapor is being driven off so that the precursor and the polymer that is formed are non-foamed products i.e. the product obtained is substantially free of voids and( solvent. Typically, precursors can be dried in two minutes as opposed to the prior art method employing a convection oven where the sample is treated at 130° C. for one hour in order to remove solvent.

The process of the invention is ideally suited for the application of a polyimide coating to any substrate and is especially adapted for coating or applying a film layer to a microcircuit or in the manufacture of sandwiched microcircuit structures. Polyimides may therefore be applied to semiconductor materials or electrical insulators and combinations of these with electrical conductors using the process and apparatus of the present invention, such process being especially adapted for the coating of alumina ceramics, glass ceramics, silica magnesium alumina, silica magnesium alumina with internal metal wiring, alumina with metal wiring and pads as well as metal lines, pads, etc. over Kapton (trademark) polyimides.

It has also been discovered according to the present invention that the process and apparatus as disclosed and described herein can be effectively used for preparing acetylene terminated polyimides in a fraction of the processing time ordinarily employed.

The key to processing the precursors for acetylene or other functionally terminated polyimides or polymers such as Thermid (trademark) 615, 601, PMR-15 (trademark) and the like (described by Bilow et al. U.S. Pat. Nos. 3,845,018; 3,864,309 and 3,879,349) lies in the ability to attain differential reactivities between the isoimide and the acetylene end groups, or the amic acid and acetylene end groups. Normally, this is accomplished by the very slow heating of the precursors. Fast heating results in the simultaneous reaction of both groups, leaving highly stressed polymeric films which have poor mechanical properties.

By employing the method and apparatus of the present invention the imidization proceeds in a controlled manner i.e., the amic acid or isoimide groups on the amic acid present in Thermid (trademark) 615 film have been almost totally converted to the imide form in three-five minutes without the reaction of the acetylene groups and almost complete solvent removal. The prior art methods of slowly heating these acetylene terminated polyamic acid materials resulted not only in the formation of polyimides hut also the polymerization of the molecule through the acetylene groups as well. Thus, a new composition of matter is obtained in that the polyamic acid groups in this class of materials is substantially converted to a polyimide having acetylene end groups that arc substantially unpolymerized and available for subsequent polymerization. This subsequent polymerization is obtained by post baking these materials in a conventional oven or microwave system, especially one having a tuneable microwave cavity or by using any other suitable heating means by which the imidization reaction is completed if not completed during the first microwave step and the acetylene end groups are reacted. Additionally, if not all of the solvent is removed in the first stage of the process it can be removed during post curing. The total processing time, (including exposing the precursor to microwave radiation according to the process of the present invention for from about three to about five minutes) is twenty minutes compared to eight hours using the prior art method.

The retention of mechanical proper ties of these acetylene terminated polyimides that are subsequently cured according to the process of the present invention can be observed from the DMTA chromatograms and stress-strain analysis, in which such materials are compared with a sample that is cured by conventional thermal means. The glass transition temperature is the same (within experimental error), the initial modulus is the same and the modulus above the glass transition temperature is the same. Furthermore, it is observed that Tg increases upon prolonged exposure at 400° C. and is exactly the same at 4° C./hour for both microwave treated and conventionally treated materials, indicating that the accelerated curing cycle of the present invention for this class of acetylene terminated polyimides is not detrimental to the mechanical properties of this material, contrary to when a very fast, high temperature thermal cure is used. Furthermore, the elongation at failure is the same, indicative of similar toughness between the microwave sample of the present and the slow thermal sample of the prior art.

Referring to the drawings, FIG. 1 illustrates a tuneable microwave resonant cavity apparatus 2 according to the present invention comprising cylindrical sidewall 4 with a topwall enclosure 6 and a bottom enclosure 8 leaving an inner surface oil which a sample of polyamic acid precursor may be) positioned. The apparatus 2 is also vented by means of opening 9 and nipples 29 in sidewall 4 or optionally elsewhere in the structure, eg. through the baseplate 8. A plate 10 is arranged to slidably engage the inner surface of sidewall 4 and has a sliding seal 11 positioned at the periphery thereof. Sidewall 4 may be constructed of stainless steel, the inner surface of which is highly polished so that it will more effectively reflect microwave radiation. The inner surface of said sidewall 4 may also be coated with a material that is highly reflective to microwave radiation but is also resistant to oxidation such as gold, silver-gold alloys and the like. The plate 10 is referred( to as a "short" and has apertures 12 arranged throughout it so that any vapor in the chambers defined above and below short 10, sidewall 4, topwall 6 and bottom wall 8 can pass through such apertures. A screen, which will also function as a short, may be used in lieu of plate 10. A conduit 20 is connected by means of nipples 29 through sidewall 4 and opens into the chamber formed between sidewall 4, short 10 and bottom plate 8. Control rods 14 are securely attached to short 10 and held in a fixed spaced relationship relative to one another by means of plate 16 having opening 18 therein, control rods 14 being slidably moveable through topwall 6 by apertures therein arranged to slidably receive control rods 14. A microwave probe 22 is slidably mounted in the base of sidewall 4 so that it may be moved in or out of the chamber defined between the bottom face of short 10 and the bottom wall 8 and sidewall 4 by means of rack 24 and pinion 26 or a threaded screw assembly operatively associated with a prime mover 28 which may be operated manually or by an electric motor controlled by a computer or manual controls. The microwave probe 22 is operatively connected at its exterior end (i.e. that end which does not project into the apparatus 2) to a microwave supply as will be further understood by reference to FIG. 2, the latter illustrating a microwave processing system 30.

The microwave power can be anywhere from 5 to 1,000 watts and especially 50 to 600 watts. A 500 watt power supply is typically used in one embodiment of the invention. Any frequency from 300 MHz to 120 GHz can be used as the microwave frequency of the microwave apparatus; specific useable frequencies are 915 MHz, 2450 MHz and 28 GHz.

Figure 2:
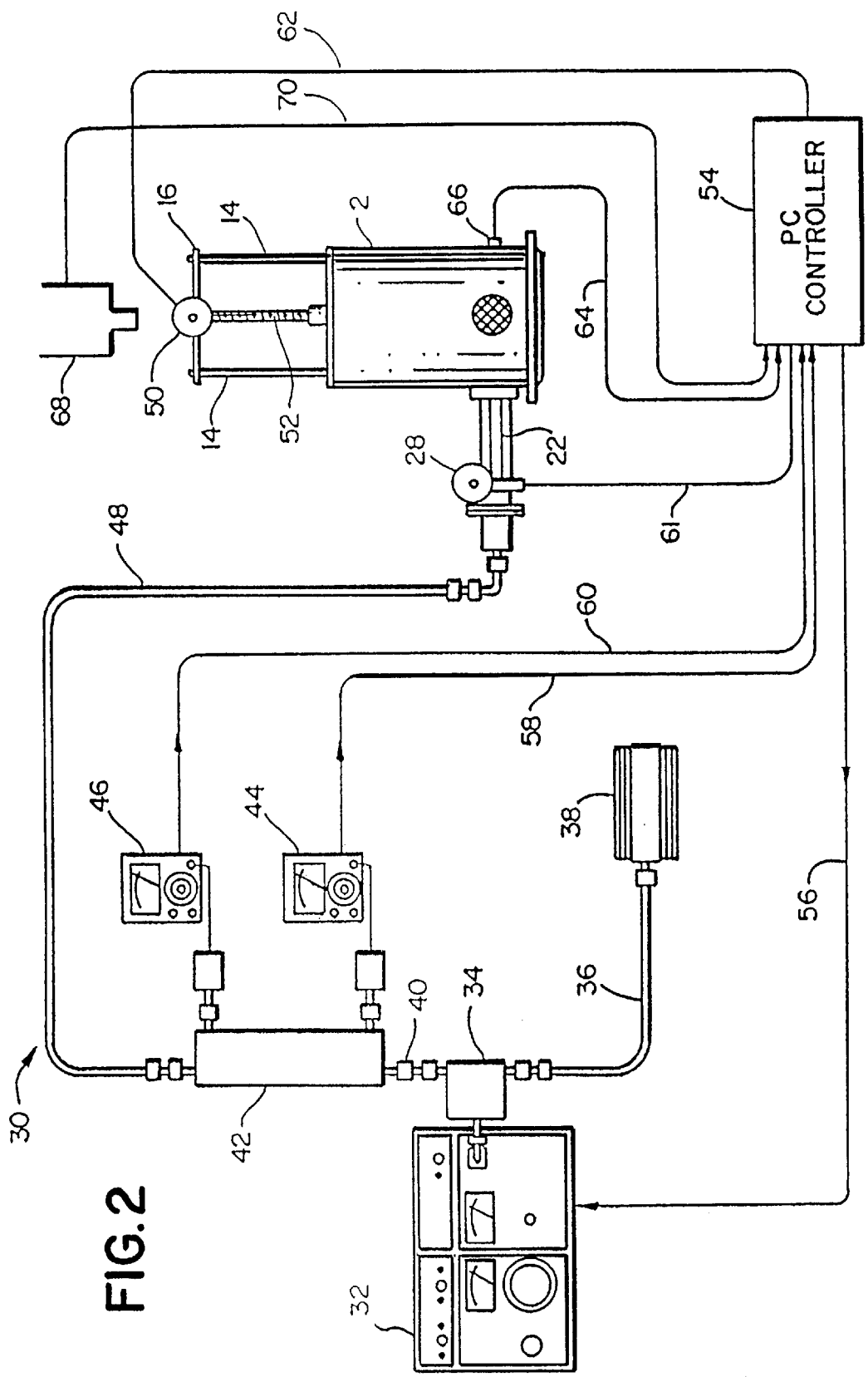
FIG. 2 comprises a flow diagram illustrating the connection to the tuneable microwave cavity of a microwave supply, three port circulator, directional coupler, power meters, dummy load, pyrometer and computer controller for monitoring power output, temperature of the workpiece and the Q factor of the microwave cavity.

The microwave processing system 30 of FIG. 2 illustrates a microwave supply 32 such as Micro-Now (trademark) model 420B1 operatively associated with a three port circulator 34 such as Ferrite control No. 2620. The three port circulator 34 has a dummy load 38 such as NARDA 368BN operatively associated therewith by connector 36. The three port circulator 34 is also operatively connected to directional coupler 42 such as NARDA 3043B which in turn is operatively associated with power meters and sensors 44 and 46 such as a Hewlett Packard HP 435 device. Directional coupler 42 in turn is operatively associated with the microwave probe 22 by means of coaxial cable or suitable waveguide 48. The short 10 as described in FIG. 1 is moved upwardly and downwardly within the device 2 by means of prime mover (e.g. electric motor) 50 operatively associated with a worm drive 52 in a manner known in the art. A controller 54 comprising a programmed computer is operatively associated with microwave supply 32 by means of conduit 56, power meters and sensors 44 and 46 by conduit 58 and 60. prime mover 28 by conduit 61, prime mover 50 by means of conduit 62 and thermocouple 66 and optical pyrometer 68 by means of conduits 64 and 70 respectively.

Figure 3:
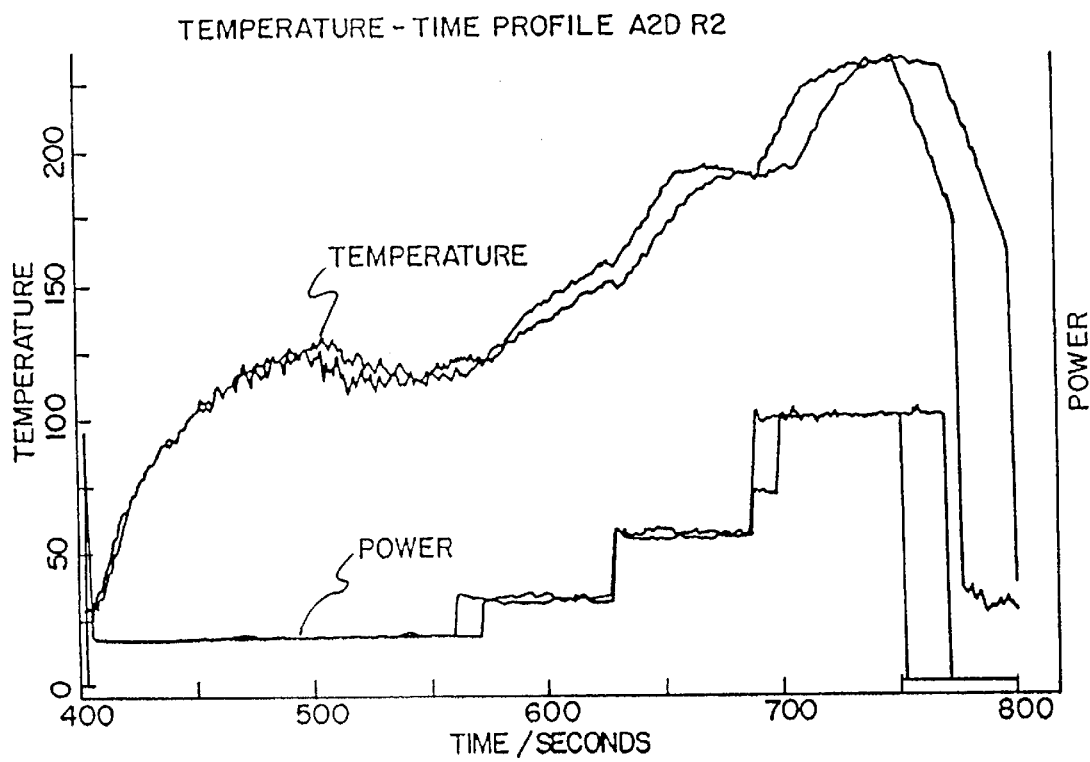
FIG. 3 is a plot of microwave power (Y axis) against time (X axis) applied to the microwave cavity of FIG. 1 and the resultant temperature of the precursor and/or polymer obtained over the period of time such power is applied for two successive runs.

In use, and referring to FIGS. 1 and 2, a polyamic acid precursor is dissolved in a solvent and coated on a base such as a microcircuit and the microcircuit thus coated positioned within the cavity between bottom wall 8, sidewall 4 and short 10 of apparatus 2. The microwave supply 32 is turned on and microwave radiation is caused to radiate from probe 22 within the chamber of apparatus 2 probe 22 being moved in or out of the chamber to match the impedance of the system as the dielectric constant of the system changes. The power is controlled by the programmed controller 54 in response to the temperature of the sample in tile chamber 2 as measured by pyrometer 68 and the temperature of the cavity as monitored by IR pyrometer 66 or an equivalent thereof. The reflected power from the apparatus 2 is measured by power meters and sensors 44 and 46 which in turn relay this information to the controller 54 which conveys a programmed response to the prime mover 50 so that the short 10 may be moved upwardly or downwardly and the probe 22 moved in and out of the microwave resonant cavity within the apparatus 2, so it may be tuned to achieve minimum reflected power and hence critical coupling for the system, as the system is defined herein. The controller 54 is programmed, in one instance to provide power to the apparatus in a manner to obtain the temperature over the time period as illustrated in FIG. 3. The application of power to attain the temperatures as set forth in FIG. 3 and movement of the short to attain the critical coupling may also be effected manually rather than by utilization of controller 54.

A feature of apparatus 2 comprises means for removing vapor from the chamber thereof so that such vapor (e.g. solvent and/or water) will not condense and redeposit on the sample being processed. As illustrated in FIG. 1, apertures 12 are provided which allow vapor developed during processing of a sample in the chamber below short 10 (as that chamber is defined herein) to pass into the upper chamber and either condense in the upper chamber or to be vented through an opening in plate 6 or by means of conduit 20 which optionally is operatively associated with a vacuum pump to more completely evacuate the chamber below short 10. Opening 9 at the bottom of sidewall 4 or nipples 29 allows for an external fluid such as dry purified dust-free air or similar gas to enter the bottom of the apparatus 2 and be withdrawn through conduit 20. Optionally, short 10 can comprise a non-perforate plate (i.e. a plate without any openings therein) and the apparatus 2 can be evacuated by a series of conduits strategically placed along the length of sidewall 4 and operated simultaneously or serially to evacuate the chamber above or below short 10 as those chambers are being varied in volume depending on the movement of short 10 upwardly or downwardly along the inner surface of sidewall 4.

The opening 18 in the plate 16 is provided so that the pyrometer 68 may be focused on the sample through an opening in top wall 6 and short 10 that is aligned with opening 18 and through which the optical pyrometer 68 may be aimed. A fiber optic temperature probe may be used in lieu of the pyrometer and focused on the sample through an opening in the sidewall 4 rather than from above.

The invention also relates to systems which have been developed that allow the computer to maintain cavity resonance by monitoring the reflected microwave power and acting so as to minimize the reflected power by the adjustment of the sliding short 10 and the input probe 22.

Initially, a system programmed into controller 54 causes the sliding short 10 to be returned to a "home" position below the desired resonance. Short 10 is then raised in a step wise manner followed by reading the reflected power after each step on meters 44 and 46. When the reflected power decreases below a threshold value, indicating an approach to a resonance dip as illustrated in FIG. 4, the step size is reduced and the direction of the step is now controlled depending on the sign of the difference between the last two data points and the absolute position of the short where those two power values were measured. As the reflected power continues to decrease below other thresholds, the step size is further reduced. If the reflected power reaches a local minimum, the computer program in controller 54 produces a signal which causes the movement of the input probe 22 so as to match the impedance of the cavity, using a similar difference between the reflected power and absolute position to determine in which direction to move to further reduce the reflected power.

This routine is capable or reducing the microwave power to less than 0.1 percent of the forward power reflected from the cavity. More importantly, the routine "tracks" a curing polymer system, resulting in the system maintaining resonance during the complete processing cycle.

A second system programmed into controller 54 requires the short 10 to move over a large distance, passing the resonance (lip, while recording the level of the reflected power and then returning the short to the position where the minimum was found. If reflected power is not zero, a similar routine, generated by processor 54 operates on the input probe 22 to Find a minimum for that axis and program execution returns to find the position of the reflected power minimum for the short period. This iteration continues until the reflected power is zero. Either this second routine or the above first routine can then be invoked to maintain resonance for the remainder of the processing cycle. Typically these routines take only about 15 seconds to find resonance.

Figure 6B:
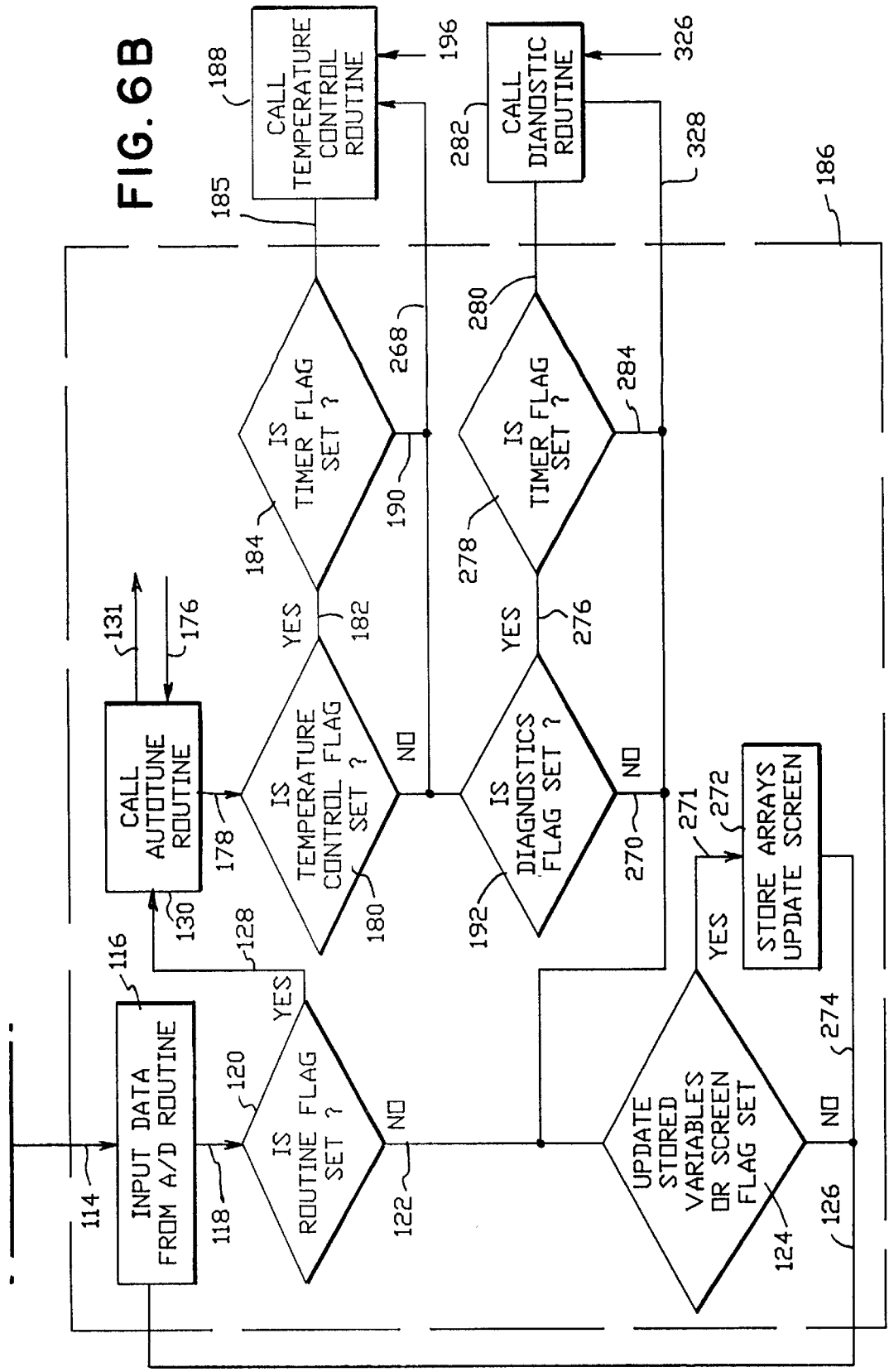
FIG. 6 is an overall flow chart of the control system of the present invention which is used to automatically control the microwave apparatus according to the present invention to achieve a desired level of microwave application to the work piece according to the present invention.

FIG. 6 shows a now chart for the design of the overall control system according to the present invention. The control system for the present invention can operate on any computer for example, an IBM 370 computer, an IBM Personal Computer, such as a PC/AT or a more sophisticated model, and any other stand alone computer having similar capability can be used. The program language used to program the control system according to the present invention can be any suitable language such as basic, fortran, assembly language, C language and the like.

Block 100 of FIG. 6 represents the system call or the command to execute the control system. Line 102 represents a signal for passage of control to block 104. Block 104 represents the initialization of the A/D convertors for power meters 44 and 46. The A/D convertors are 16 channel A/D convertors (model number DAS-16 manufactured by Metrabyte). The A/D convertors need at least three inputs, one for temperature, one for incident radiation power and one for reflected radiation power. Directional coupler 42 strips off 1% of the input power and 1% of the reflective power and directs into meters 46 and 44 respectively (these meters are Hewlett Packard Microwave Power Sensor meters Model Number HP 435 B) When the A/D convertor is first initialized the multiplexer is set up to read at a predetermined repetition rate specified in the program the incident and reflected power at preferably from 20 to about 30 times per second. Temperature is monitored by pyrometer 68 which is fed into the A/D convertor or alternatively communicates to the controller via a RS-232c interface or similar. The input to the A/D convertor from meter 44 is line 58, the input from meter 46 to the A/1) convertor is line 60 and the input from pyrometer 68 to the A/D convertor is line 70 of FIG. 2. The output from meter 44, meter 46 and pyrometer 68 produces an input to the A/D convertor which generates a signal indicative of input power, reflected power and temperature in the computer on which the control system is running. Block 104 also corresponds to initializing the timer of the computer to correspond to the running time of the program. Every $\frac{1}{18}$th of a second corresponds to one count in the timer. Therefore, the counter which is initialized at the beginning of the call of the program to zero is incremented one at every $\frac{1}{18}$th second time interval. Block 104 corresponds to setting up of the following interrupts which are used during the running of the control system. Set system timer interrupt to point to a subroutine which counts events. When sufficient counts have been received to allow an event (e.g. plot the data on the screen) a flag is set in the interrupt routine, which is then read and acted on accordingly by the program during normal operation. After execution of the interrupt subroutine, program execution resumes at the point at which the interrupt occurred.

The controller 54 of FIG. 2 interacts with prime mover 28 of probe 22 and prime mover 50 of short 10 by means of a standard serial interface digital communications port RS232C for output to stepper motors (model Number 57–51 fabricated by Compumotor) used for the prime movers 28 and 50.

Line 106 rep resents a sign al passage of system control to block 108. Box 108 represents presentation of an options screen on a display means such as the CTR display of an IBM Personal Computer. Creation of option screens in C language is described in, for example, Borlond Turbo C Reference Guide (Borland International) Any reasonable number of options are presented at this level, of which seven are activated and can be selected by the operator of the control system. Option one controls the output to a display terminal which plots temperature versus time, forward power versus time, and reflected power versus time. The scale of the vertical and horizontal axis arc set in option one. Option two controls a plot of the Q of the cavity versus time. The horizontal and vertical axis of the Q versus time plot arc controlled in option two. In option three the sensor from which the temperature versus time data for the plot of option one can be set. In the preferred embodiment, only one monitor of temperature for the work piece is utilized in the control routines described herein below. Option four specifies that only the data of temperature, forward power and reflected power are to be acquired versus time without a call of the temperature control routine or the diagnostic routine both of which will he described herein below with reference to FIGS. 8 and 9. In option 5 the automatic tuning routine only can be selected in order to minimize reflected power without running the temperature control routine or the tune diagnostic routine as defined herein below, while simultaneously acquiring the data described in option 4. In option 6 the operator can select running of tee temperature control routine and the automatic tuning routine without selecting of the diagnostic routine. In option 7 the operator can select the diagnostic routine, the temperature control routine and the auto tune routine, which) is defined ,is the complete control system.

Figure 10:
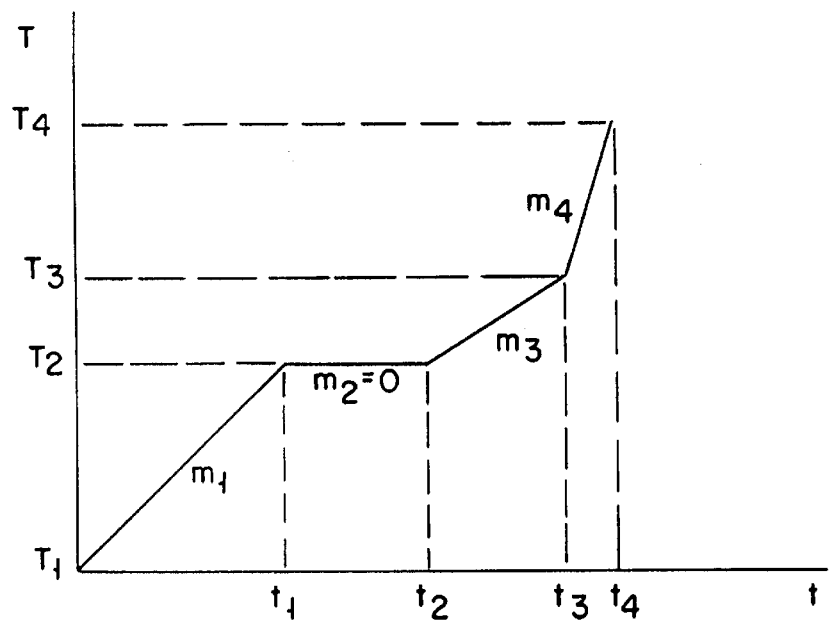
FIG. 10 is a typical temperature time profile showing the manner in which segments are used to input the desired profile to the program.

The temperature control subsystem as will be described in greater detail herein below, looks to a data set which contains data for the applied temperature versus time schedule. For example, FIG. 10 shows schematically a plot of a temperature versus time schedule. The data for this is placed in a data set which has groups of three numbers. The first number being a initial temperature for the first time interval, the second number being the linear time rate of change of the temperature and the third number is the time of duration of a constant temperature hold or soak. Referring to FIG. 10 the data read from a file corresponding to the versus time schedule of FIG. 10 would be: 7; $T_1$, $m_1$, $t_2$-$t_1$; $T_2$, $m_3$, O; $T_3$, $m_4$, O. The times $T_2$-$t_1$ as necessary are determined by the current value of the counter described herein above. For the time interval between time $t_1$ and $t_2$ the time rate of change of temperature with respect to time $m_2$ equals 0 which means that the work piece is held a temperature T2 for a time $t_2$-$t_1$ which is commonly referred to as a soak or a hold at temperature $T_2$. The referred to change of temperature with respect to time can have values which are positive, negative and 0.

As represented by block 104 every 1/18th of a second the program sets up a flag which increments the counter so that the program can keep its own time. The measured data for temperature, forward power and reflected power is saved and the screen to which the plots can be made is updated once per second. Therefore, once every second an additional data point is added to the plot which is on the screen to eventually completely fill out the plot. The determination of Q is done once every 5 to 30 seconds (the frequency at which Q is determined, that is once every X number of seconds is determined from option 2, box 108). The time is determined by the value n in the counter where the actual time is N X 18. When N is 18 this corresponds to one second. The time interval at which Q is evaluated is set by typing a number onto tile screen presented as a result of block 108. If no value for this time interval is entered, a default valve is loaded.

Line 110 represents a signal for transfer of program control from block 108 to block 112. Block 112 presents the screen on which the plots referred to herein above are presented. On the upper left hand corner of the screen is a list of the options including start run, save data, change microwave power, start/stop auto tune routine and change stepper motor increments (for manual) movement of stepper motors (28 & 50 in FIG. 2) At the upper right hand corner of the screen is presented the current value of the data which is being plotted on the screen that is the current temperature, forward power, reflected power and heating rate. At this screen there is a hold which is waiting to be released by the press of a key stroke to permit the program control run to start.

FIG. 3 is the type of plot which is plotted on the display screen when all of the data is acquired. The plots of FIG. 3 are built up over time with the data being updated once every second. At block 112 other options other than to start a run can be selected. These can be conveniently controlled by the F keys on the key board of an IBM Personal Computer. Other options besides program start can be to save the data into a data set or data location, turn off or on the auto-tuning routine no matter which options have been previously selected at block 108 and select the radiation power to be applied directly from the keyboard. Other options are within the scope of the art and can be added at this point of the control routine. How to control the F keys and display plots at the terminal can be found in any language manual, e.g. Turbo C Reference Guid Version 2.0 from Borland International. At block 112 motor 50 controlling short 10 is advanced to move the short as close to the work piece as possible. Motor 28 is advanced to withdraw antenna 22 as far out of the cavity as possible in order to find the zero of the location of the antenna and it is then advanced in towards the workpiece to an average position which has been previously determined by experimentation to be a preferable starting position to the location of antennae 22 for the minimum power reflection. The actual position of this antenna does not need to be known accurately since the control program automatically optimizes this position. The approximate value of the starting position can be found by operator intervention or using the position for the empty cavity.

Line 114 represents a signal for transfer of system control to block 116. Block 116 represents the system receiving data from the A/D convertors which receive input signals from forward and reflected power monitors 46 and 44 and from pyrometer 68. Data is continuously fed into the system controller as signals indicative of the applied power level, the reflected power level and the temperature of the sample as part of block 116. Line 118 represents a signal for transfer of program control to block of 120.

In block 120 there is a test made to determine if the autotune flag was set in order to call the autotune routine. The autotune routine nag is set in block 108 as previously described. If the autotune subsystem flag has not been set, system control is passed by a signal represented by line 122 to block 124 where a test is made to determine if the screen flag is set and whether the flag to update stored data variables is set by the interrupt subroutine. IF the flag to update store variables or to update the screen is not set program control passes from block 124 by a signal which is represented by line 126 back to block 116.

Figure 7:
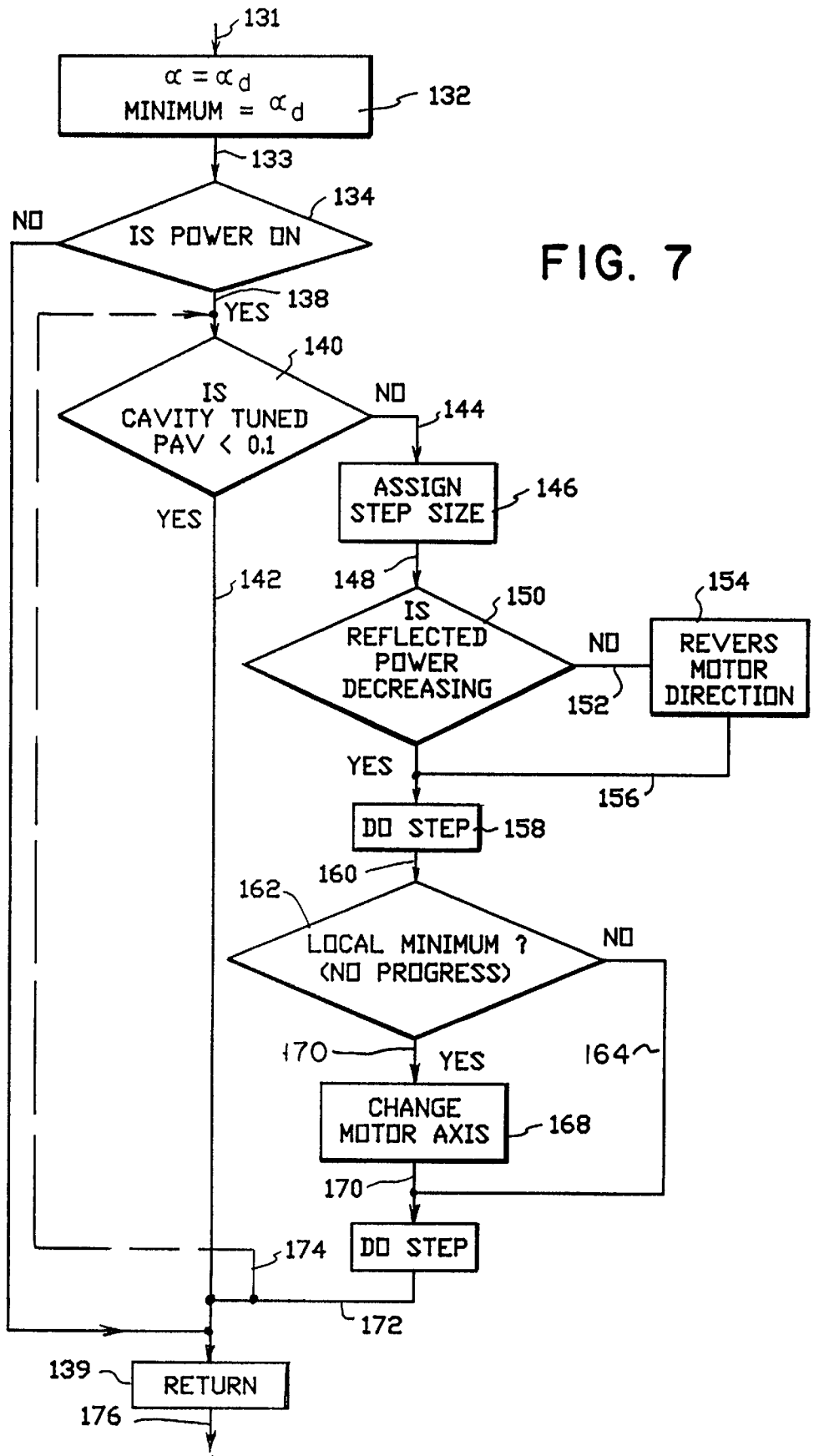
FIG. 7 is a flow chart of the autotune subsystem of the system of FIG. 6.

Returning back to block 120 if the autotune nag is set. (Typically being set is to be set to one) program control passes from block 120 by a signal as represented by line 128 to block 130 which is a call to the autotune routine which is shown in FIG. 7. Transfer of program control to the autotune routine is by a signal represented by line 131.

FIG. 7 is a flow chart of the autotune subsystem of FIG. 6. In the autotune subsystem, the position of a microwave antenna such as 22 of FIG. 1 and the position of a short such as 10 of FIG. 1 are adjustable. There are means for receiving a signal indicative of the positions of the antenna and short and means for generating a signal for changing the position of the antenna and short.

Line 131 of FIG. 7 represents the call to the autotune subsystem which leads to block 132 α is set to the value of the ratio of the reflected power to the forward power. In block 132 the first of the group of the short and the antenna to be moved to tune to cavity is defaulted to the short. At block 134 a test is made to determine whether the radiation power is on. If the radiation power is not on program control is transferred by a signal as represented by line 136 to box 139 which is the return signal as represented by line 176 to block 130 which is the call to the autotune routine. If at block 134 as a result of the test it is determined that the microwave power is on, program control is transferred by line 138 to block 140. At block 140 a test is made to determine whether the cavity is tuned. The cavity is defined to be in tune if a is less than a predetermined value preferably 0.1%. If the cavity is found as a result of this test to be in tune, program control is transferred by a signal as represented by line 142 to block 139 which is the return to a block 130 of FIG. 6 which was the call of the autotune routine. If the cavity is not in tune, system control is transferred by a signal as represented by line 144 to block 146.

In block 146 the step size for the prime moves 28 and 50 of FIG. 2 are set according the following equations. The prime movers are motors Compumotor, Model 57–51 which make 12,800 steps per 360° of rotation. The total number of steps advanced based on the test of $\alpha$ is called the increment. The test is as follows: if $0.1 \leq \alpha < 0.25$ then the increment is 50 steps; if $0.25 \leq \alpha < 0.4$ than the increment is 80 steps; if $0.4 \leq \alpha \leq 0.65$ than the increment is 130 steps; if $0.65 \leq \alpha \leq 0.8$ than the increment is 180 steps; and, if $0.8 \leq \alpha \leq 1$ than the increment is 250 steps. Optionally, the increment can be set equal to the ratio of reflected power to the forward power ($\alpha$) times a constant plus an offset wherein the constant and the offset arc inputs which can be input at the option screen represented by block 108 of FIG. 6. control is passed from block 146 by a signal as represented by line 148 to block 150. In block 150 a test is made to determine whether or not the reflected power is decreasing or is not decreasing. If the reflected power is not decreasing, that is the current value or reflected power is greater than the previous value of reflected power, program control is passed by a signal as represented by line 152 to block 154 which sends a signal to the prime moving means 28 or 50 which is currently being controlled to reverse direction. System control is transferred by a signal as represented by line 156+160 to block 162. In block 162 a test is made to determine whether the current value of reflected power is at a local minimum. If the current value of $\alpha$ is less than the value of MINIMUM then MINIMUM is updated to the current value of $\alpha$ and a variable COUNT is set equal to zero. If the current value of $\alpha$ is not less than MINIMUM then MINIMUM is not updated and the variable COUNT is set equal to COUNT +1 (count=0 in Box 104, minimum is set to a large value in box 104). If count is not greater than some predetermined value, preferably 15, it is determined that there is NO local minimum and program control is passed by a signal from block 162 as represented by line 164 to block 158. At block 162 if COUNT is greater than 15 then it is determined that there is a local minimum and system control is passed by a signal as represented by line 166 to block 168 which changes the control of the prime mover from 50 to 28 or from 20 to 58, thereby changing the axis which is being adjusted in order to automatically tune the cavity. From block 168 program control is passed by a signal as represented by line 170 to block 158 which executes the increments as determined in block 146 on the axis determined in blocks 162 and 168 in the direction determined in blocks 150 and 154. Program execution is then passed to block 139 which represents a return to block 130 in FIG. 6. Optionally, a signal as represented by line 172 rather than returning directly to block 138 could as represented by dash line 174 return to block 140, thereby avoiding a return to the main routine of FIG. 6 until the cavity satisfies the $\alpha$ condition of block 140 resulting in a signal to transfer program control as represented by line 142 to block 139 for a return to block 130 of the main program in FIG. 6.

The signal output from Block 130 to the autotune routine is represented by the line 131 the input signal from the autotune routine to block 130 is represented by line 176.

Returning to FIG. 6 system control is passed by a signal from block 130 after the call to the autotune routine as represented by line 178 to block 180 which tests if the temperature control flag has been set at block 108. If the temperature flag is set, program control is transferred by a signal as represented by line 182 to block 184 which tests if the timer flag has been set. The timer flag is set in the interrupt subroutine. There is a test at this point to make a decision as to whether to call the temperature control routine. The data acquisition as represented by block 116 is done 20 to 30 times per second. The temperature control routine is not done as frequently. The data acquisition and the autotune routine are contained within dashed line 186. The sequence of controls and signals within outline 186 are executed 20 to 30 times per second. If the temperature control routine were called this frequently the system would attempt to over control the temperature. The temperature control routine is preferably called from 1 to 2 times per second. Therefore, the data acquisition segment of the system represented by outline 186 is called more often. As described hereinabove the time counter is updated every $\frac{1}{18}$th of a second to call the temperature control routine twice every second the temperature control routine will be called when the time counter is evenly divisible by 9. If the time counter is easily devisable by 9, program control is transferred by a signal as represented by line 185 to block 188 which is the call to the temperature control routine. If the time counter is not evenly divisible by 9 the system control is transferred by a signal as represented by line 190 to block 192. Line 194 emanating from block 188 represents a signal for transfer of system control from block 188 to block 198 of FIG. 8.

At block 198 a test is conducted to determine whether or not the temperature is in a hold condition (referred to as a hold or soak temperature) as designated by the temperature schedule input as defined herein above. If the temperature according to the temperature schedule is in a soak condition, program control is transferred by a signal as represented by line 200 to block 202. In block 202 the current time is compared to the time at which the soak began, to determine the time already spent in the soak mode. System control is transferred from block 202 by a signal as represented by line 204 to block 206. At block 206 the current soak time is compared to the time as designated by the input temperature schedule to determine if the current soak time is greater than the desired time to be in soak as determined from the temperature time input schedule.

The soak flag is initialized to a value of zero in block 104 of FIG. 6 which represents not being in a soak. If the soak flag is equal to one it represents being in soak.

At block 206, if the current time is greater than the time desired to be in soak, programming control is transferred by a signal as represented by line 208 to block 210 in which the soak nag is reset to zero representing a condition of not being in soak. From block 210 as represented by line 212, program control is transferred by a signal to block 214. In block 214 there is a test to determine if the temperature has reached the end of the temperature time input schedule which occurs if there are no more segments of the temperature time input schedule. This can only be achieved if a final pass has been made through block 210 which resets the soak flag to off. If the temperature program is not complete, system control is transferred by a signal from block 214 as represented by line 216 to block 218 which is the return to the temperature control routine call of block 280 as represented by line 196 on FIG. 8 and FIG. 6. Since, when the program passes control from 214 via line 216 to block 218 the temperature control flag is still set to one or yes, the program control cycles through the remainder of the stream represented by block 186 of FIG. 6. This includes passing through block 180 with the temperature control flag still set to one or yes with the system control passing to block 184 as represented by line 182.

Returning to FIG. 8, if the temperature control schedule is complete, that is, there is no more data to be read from the input control schedule, the system control is passed from block 214 by a signal as represented by line 220 to block 222 which resets the end of program flag which was initialized in block 108 to be one. At block 222 of FIG. 8 the end of program flag is set to zero which is a signal for the program to stop so that when system control is transferred by a signal from block 222 as represented by line 224 to the return 218 through a signal represented by line 196 to the temperature control call 188 of FIG. 6, the system control cycles through the routine contained within dashed outline 186 of FIG. 6 and reaches block 116 by a signal represented by line 126. At block 116 the end of program flag will be zero and the program will end. Alternatively, program execution could return to, for example, block 108 to await new option settings, etc. Returning to FIG. 8 if at block 198 the soak flag is set to zero, program control is passed by a signal as represented by line 226 to block 228. By having a single test, the program flow is simplified, e.g., if the next stage is a ramp (not soak) the program will move on after passing through block 198 (with soak=0). By looking at the initial temperature of the next input "segnment" (which consists or up to one ramp and one soak) we can allow for cooling profiles and cycling, if necessary. the current temperature is greater than the next temperature soak, system control is transferred by a signal as represented by line 230 to block 232 which sets the soak flag equal to one or yes. System control is transferred by a signal from block 232 as represented by line 234 to block 236. At block 236 the initial time for the beginning of the current soak is recorded—this corresponds to the time as recorded in the time counter for each pass through block 236 which only occurs when a soak in initiated. System control is transferred by a signal from block 236 as represented by line 238 to block 202. At block 202 the current time is compared to the initial time set in block 236 which is compared with the desired time in soak. The times in the temperature profile only include the soak times (set to 0 if no soak). This is the only point at which a time comparison is made and only applies for the time in soak. System control is passed by a signal from block 202 as represented by line 204 to block 206 where a test is made to determine if the time in soak is greater than the desired time. If the time in soak is greater than the desired time system control is passed by a signal from block 206 as represented by line 208 to block 210 as described herein above. If the soak time is set to zero—no soak required, program execution will move to block 210, via line 208 to reset the soak flag, as described herein above. If the current time in soak is not greater than the desired time in soak the system control is passed from block 206 by a signal as represented by line 240 to block 242 where a test is made of the current value of temperature with the desired temperature during the current segment of the temperature time schedule. If the temperature is not different than the temperature desired, the system control is passed from block 242 as represented by lines 244 and 212 to block 214. If at block 242 the temperature is different than the desired temperature, system control is passed from block 242 as represented by line 246 to block 248. At block 248 a test is made to determine if the temperature is greater than or less than the desired temperature. If the temperature is less than the desired temperature an output signal is sent from the control system to the microwave source 32 along signal line 56 from the controller 54 shown in FIG. 2. If the current temperature is higher than the desired temperature the output signal is indicative of decreasing the power output of radiation source 32. If the current temperature is lower than the desired temperature the output signal is indicative of increasing the output power of the radiation source 32. A number or temperature control algorithms could be used but the preferred method follows: the power is changed according to the following relationship:

$$\text{new power} = \text{current power} \times \text{desired} \frac{\text{temperature}}{\text{actual}} \text{ temperature}$$

control is transferred from block 248 by a signal as represented by line 250 and 212 to block 214. The remainder of the temperature control routine will pass block 214 as described herein above.

Figure 8:
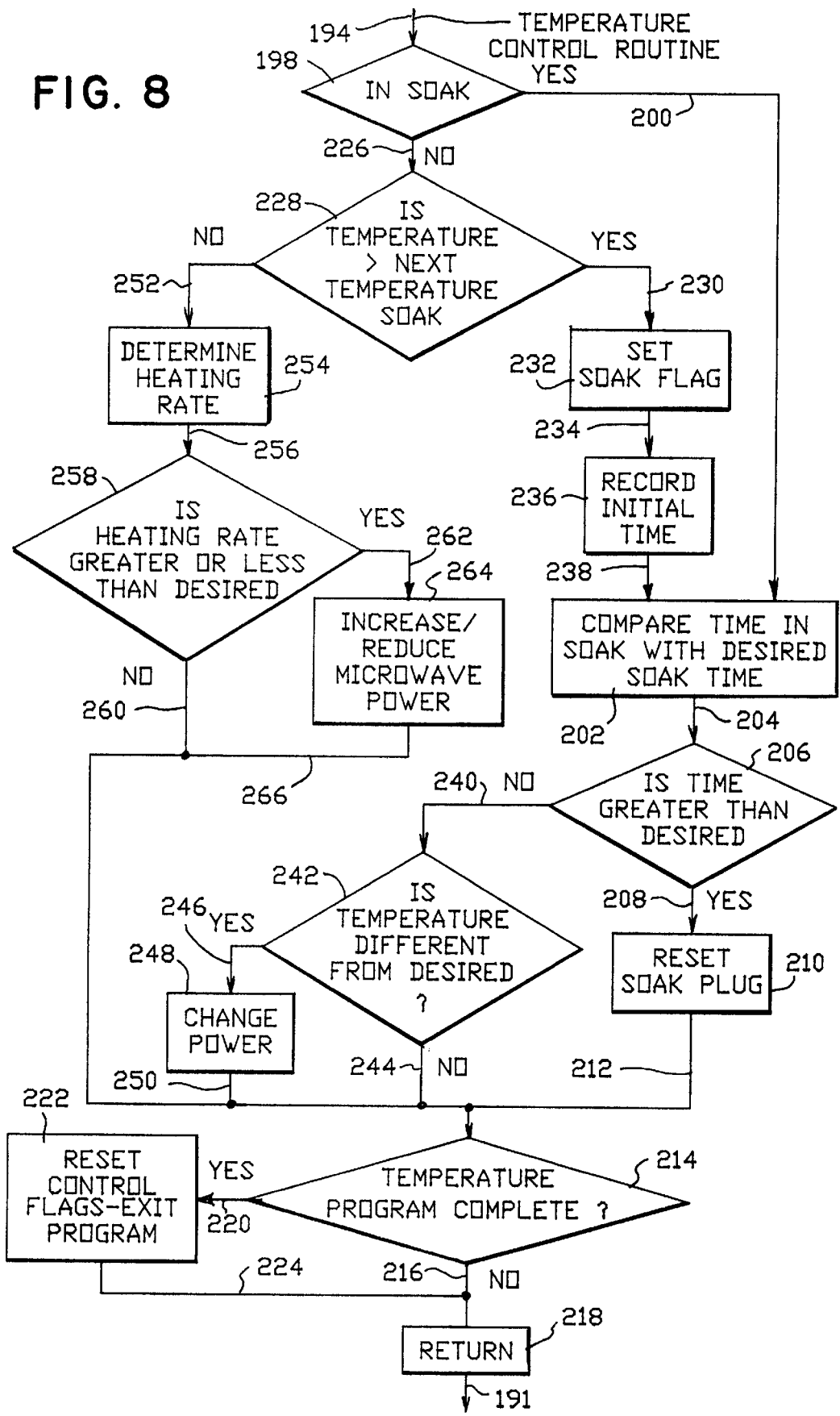
FIG. 8 is a flow chart of the temperature control subsystem of the system of FIG. 6.
Figure 9:
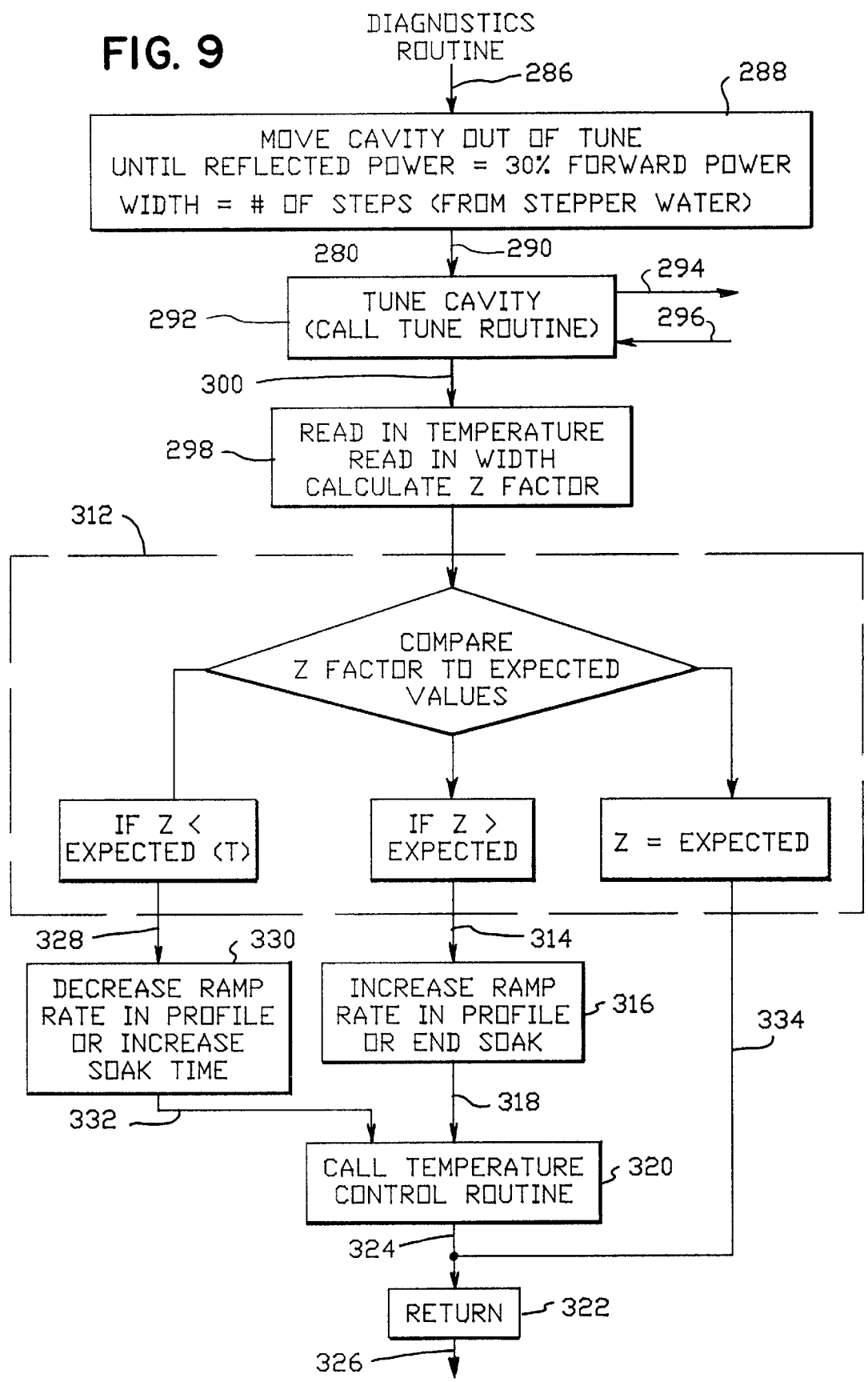
FIG. 9 is a flow chart of the diagnostic and end point detection subsystem of the system of FIG. 6.

Returning to block 228 of FIG. 8 if the current temperature is less than the next soak temperature, system control is transferred from block 228 by a signal as represented by line 252 to block 254. In block 254 a least squares linear fit is made to preferably five consecutive data points of temperature versus time to determine the heating rate. After the heating rate is determined, system control is passed by a signal as represented by line 256 to block 258. In block 258 a determination is made as to whether the heating rate is greater or less than desired. If the heating rate is not greater or less than desired, system control is passed by a signal as represented by line 260 to block 214. If the heating rate is greater or less than the desired heating rate, system control is passed from block 258 by a signal as represented by line 262 to block 264. The desired heating rate is the heating rate specified in the time/temperature schedule from the input data set as described herein above. In block 264 the power output of the radiation source 32 of FIG. 2 is increased or decreased as follows: new power is equal to the present power times the ratio of the current rate to the desired rate. An alternate method is to increment the power by a fixed amount for example 5 Watts which can be set at block 108 of FIG. 6. At block 264 a signal indicative of the increase or decrease in the current power output of radiation source 32 is controlled by a signal transmitted from controller 54 of FIG. 2 along line 56 to an input on radiation source 32 via a 0–10V input, 10 V corresponding to full power. The signal voltage is generated by the digital to analog section of the DAS-16 (Metrabyte) card disclosed above. The desired change in power is made at block 264 and system control is passed by a signal as represented by line 266 to block 214. The remainder of the temperature control routine From block 214 onward is described herein above.

System control passes from the return block 218 of FIG. 8 of the temperature control routine by a signal as represented by the line 196 to block 188 of FIG. 6. System control is transferred by a signal from block 188 as represented by line 268 to block 192 which tests whether the diagnostic flag has been set. If the diagnostic flag has not been set, system control is passed by a signal as represented by line 270 to block 124. In block 124, it is determined if the current values of the temperature, time, forward p)wer and reflected power should be stored in memory locations and the plot on the screen set up at block 112 updated. If this is the case, program execution transfers using line 271 to block 272 and the data of the current data points is updated on the screen set up at block 112 as described herein above. System control passes by a signal from block 272 as represented by line 274 and line 126 to block 116 at which point the program will stop if the program control flag is set to zero or off.

Returning to block 192, if the diagnostic flag is set to one, system control is passed by a signal as represented by line 276 to block 278. In block 278 there is a test to determine if the timer flag is set. Since the diagnostic routine takes a few seconds to run it is called substantially less frequently than the temperature control routine or the autotune routine. The diagnostic routine is called every five to thirty seconds. As described hereinabove when the time counter is at 18 this corresponds to one second, therefore, if the diagnostic routine is called every five seconds program control is transferred by a signal from block 278 as indicated by line 280 to block 282 when the counter has a value equal to N×5×18 where N is an integer.

If this condition is not satisfied, system control is transferred by a signal from block 278 as indicated by line 284 to block 124 and system execution from block 124 onward is as been described hereinabove. If program control is transferred to block 282 the diagnostic routine is called and the system control is transferred by a signal as indicated by line 286 to block 288 of FIG. 9. At block 288, the system sends a signal to prime mover 50 indicative or moving short 10 closer to the workpiece until the system receives an input from meter 44 indicating that the reflected power is 30% of the signal received from meter 46. They are the minimum step size of the stepper moter. The Q of the cavity is conventionally determined from the width of the reflected power at half height. However, we have determined that a value can be obtained which is analogous to the Q by measuring the width at less than half height. The Q of the cavity then is taken as two times the distance with the short had to be moved to place it 30% out of tune. Block 288 therefore corresponds to the determination of the current value of Q. System control is transferred from block 288 by a signal as indicated by line 290 to block 292. The cavity is now tuned again by calling the tune routine. The system will cycle in the tune routine until the reflected power is less than 1% of the forward power. After the cavity has been returned, system control is returned to block 292. System control is transferred from block 292 to the tune routine as indicated by line 294. System control returns by a signal to block 292 from the tune routine as indicated by line 296. System control is transferred from block 292 to block 298 as indicated by line 300.

Figure 11:
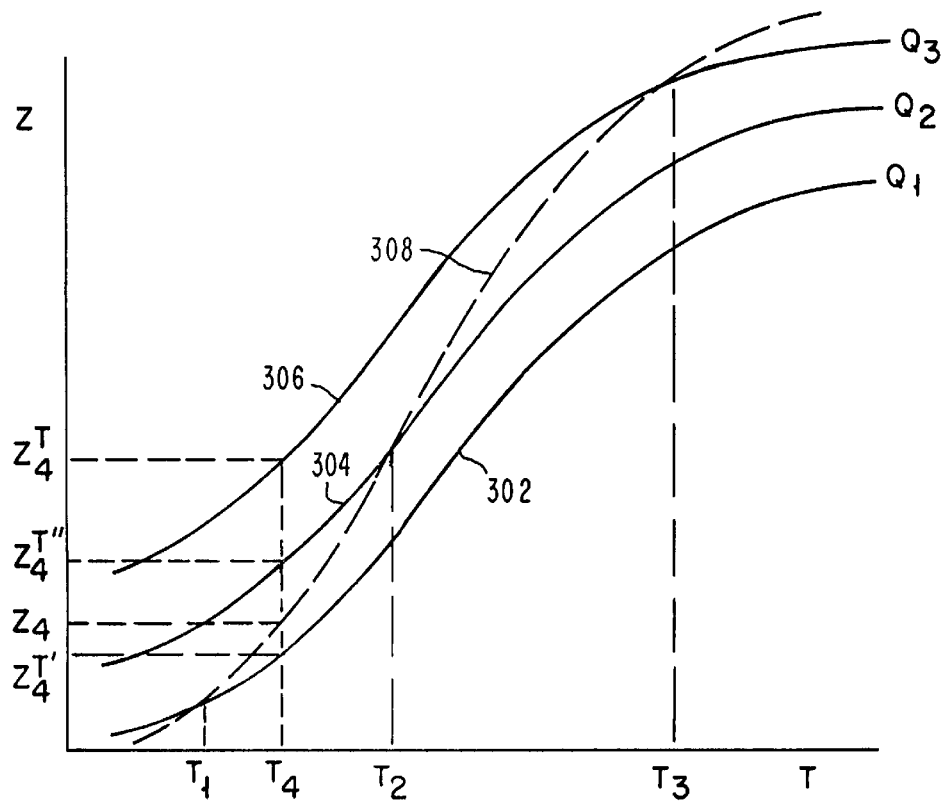
FIG. 11 shows the dependence of Q on Z and Temperature.
Figure 13:
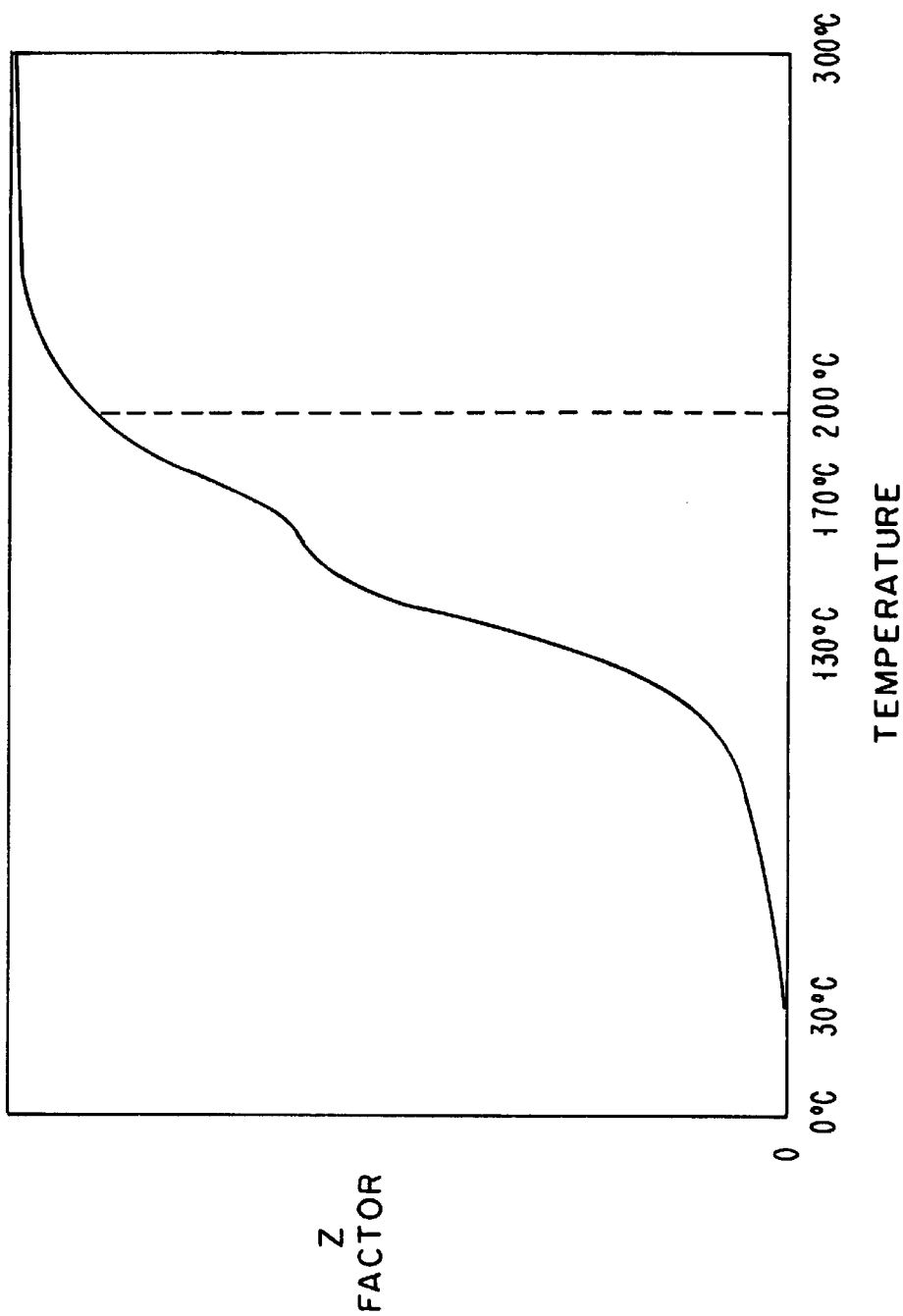
FIG. 13 is a plot of a typical Z-factor versus temperature profile as monitored during a curing process.

As described hereinabove an empirical Z factor is determined by experimental measurements. Z corresponds to the percent of cure of the sample for example, if the workpiece is a polyamic acid which is being cured to a polyimide Z corresponds to the percent cure to polyimide. The relationship between Z and Q and T can best be determined by processing the sample to a point stopping the microwave radiation to allow the sample to cool without causing further changes in the physical or chemical processes occurring during processing. During this time, Q and T are monitored (by turning the microwave on at low power for a short time). This process is then repeated and the results fitted to a curve to give Z=f(Q,T). This represents the empirical data to which an equation can be fit to determine a function wherein Z=f(Q,T) wherein f is determined by curve fitting to the data. Where it is known from an analysis of the empirical data that there are regions of the Q–T data wherein Z changes rapidly, a preferred Z versus T history can be determined. This is schematically represented in FIG. 11 by curve 308 wherein curve 308 is the Z versus T history that is preferred or the expected history which is desired to be achieved in order to most efficaciously operate on the workpiece. For example, in the case of the cure of a polyamic acid to a polyimide as described herein above, there are two regions within which Z changes rapidly as can be seen in FIG. 13 and within which it is desirable to control Z more carefully, that is, drying the solvent from the polyamic acid and curing the subsequent polyamic acid free of solvent to the polyimide. In the remainder of this discussion the expected Z refers to a generic curve of the type designated as 308 shown in FIG. 1.

At block 298 the current temperature and the current Q are used to evaluate the current Z factor. The current Z factor shall represent the Z factor which is determined from the equation or data list which is based upon empirical observations. System control is passed by a signal from block 298 as represented by line 310 to block 312. In block 312 the current A factor is compared to the expected or desired Z factor for the current temperature. If the current Z is greater than expected, system control is passed by a signal from block 312 as represented by line 314 to block 316. Block 316 controls an output signal indicative of changing the power output of radiation source 32 by sending a signal from controller 54 along line 56, since the current Z shows that physical conditions are ahead of the expected Z. If the current segment temperature versus tine profile has a temperature ramp, this ramp is increased in order to exit this segment of the temperature versus time profile more quickly, or if this segment of the temperature versus time profile is a soak condition, the soak is ended to exit this segment of tile time versus temperature profile more quickly. System control is transferred by a signal from block 316 as indicated by block 318 to block 320 which is a call to the temperature control routine to continue onto the next segment of the temperature versus time profile. System control is transferred by a signal from block 320 to block 322 as indicated by line 324. Block 324 is the return to block 282 of the main routine of FIG. 6 wherein line 326 represents the return signal to the block 382.

Returning to block 312, if the current value Z is less than the expected value of Z the current physical conditions are behind the expected conditions and system control is transferred by signal from block 312 as indicated by line 328 to block 330 which sends out a signal from controller 54 along line 56 to radiation source 32 of FIG. 2 which is indicative of decreasing the ramp rate in the input profile in order to extend the time in the current segment of the temperature versus time profile or to increase to soak time in order to extend the current time spent in the soak segment of the temperature versus time profile in order to permit the current Z to come up expected value of Z. Program control is transferred from block 330 as indicated by line 332 to block 320. Progress of the system from block 320 on is described hereinabove. Returning to block 312 if the current Z is equal to the expected Z system control is transferred by a signal from block 312 as indicated by line 334 to block 322 which transfers control by a signal as indicated by line 326 to block 282 which calls the diagnostic routine. System control is transferred by a signal from block 282 as indicated by line 328 to block 272. Progress of the program after block 272 is as described hereinabove.

Figure 12:
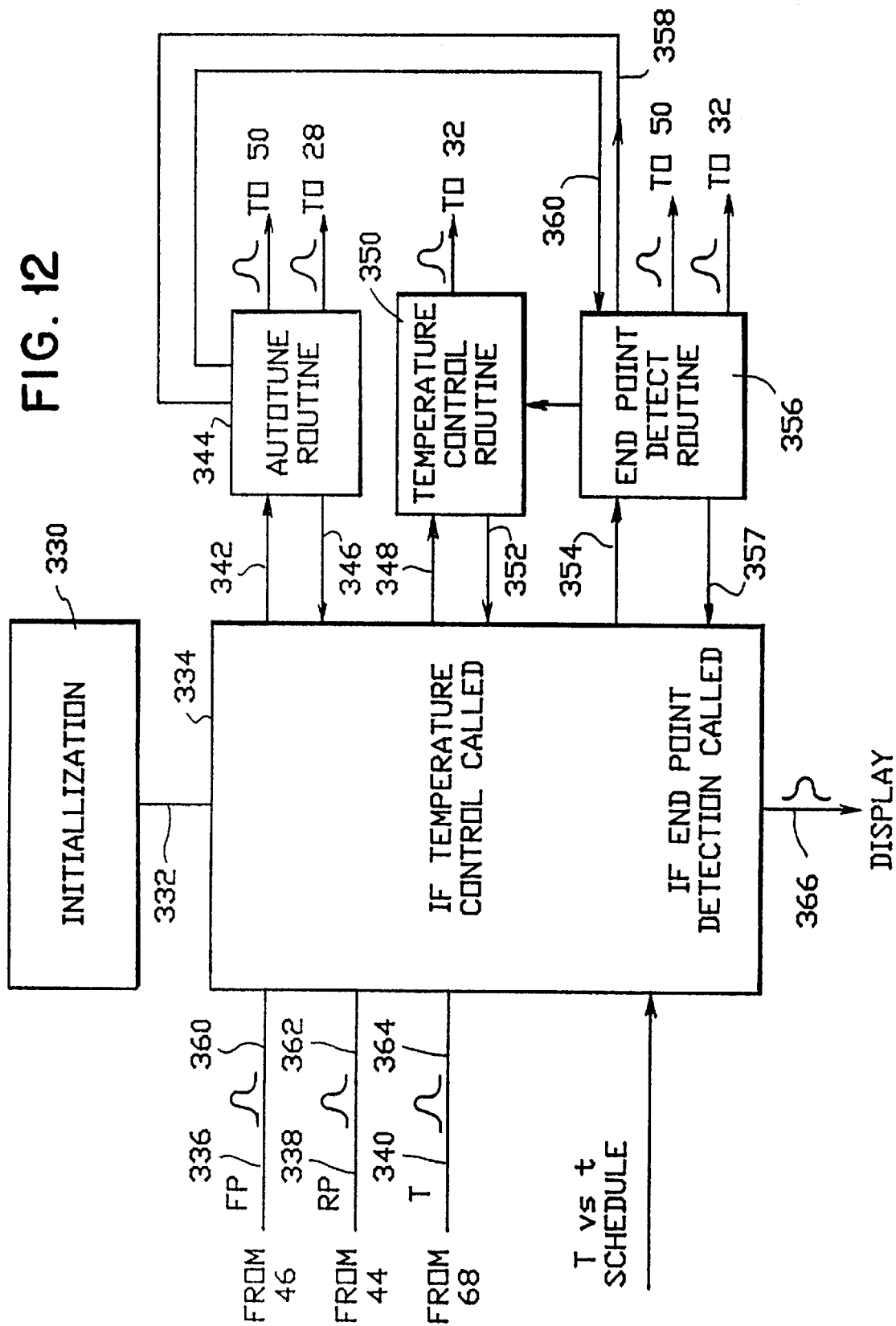
FIG. 12 is a logic block diagram showing the interconnection between subroutines for tool control.

FIG. 12 shows a schematic diagram summarizing the control system shown in detail in FIGS. 6, 7, 8 and 9. Block 330 represents the initialization of the program which includes elements 100, 102, 104, 106, 108, 110, 112 and 114 of FIG. 6. line 332 represents transfer of control by a signal from block 330 to block 334 which represents the data acquisition and display function of the control system. Block 334 receives a signal as indicted by line 336 indicative of the forward power, FP, from meter 46 of FIG. 2. Block 334 receives a signal as represented by line 338 from a meter 44 of FIG. 2 indicative of the reflected power. Block 334 a signal receives from temperature monitor 68 of FIG. 2 as indicated by line 340 indicative of the current temperature of the workpiece. System control is transferred by a signal From block 334 as indicated by block 342 to autotune subsystem of block 344. From the three input signals a test is determined as to whether the ratio of reflected to forward power is less than a predetermined value, preferably 0.01. If this condition is satisfied, system control is transferred by a signal back to the data acquisition and display function of block 334 as indicated by block 346. If the test of whether the cavity is in tune is not satisfied, first a signal indicative of how to move short 10 of FIG. 2 is sent to prime mover 50. If a local minimum in the reflected power is found after moving the prime mover 50, the signal indicative of how to move prime mover 28 to control the location of the antenna is provided to minimize the reflected power with respect to the antenna 22 of FIG. 2. (Movement of the antenna and short can be done in any order and can be repeated any number of times.) When a tune condition is satisfied, system control is returned by a signal from block 344 as indicated by line 346 to the central control system as represented by block 334. The central control system reads in a temperature versus time schedule. The temperature control is called, system control is transferred by a signal from block 334 as indicated by line 348 to block 350 which is the temperature control routine. If the end of the temperature versus time schedule has been reached the system control is transferred from block 350 as indicated by line 352 to the central control unit 334 and the system ends. If the end of the temperature versus time schedule has not been reached a test is made to determine if the current temperature is a temperature indicated by the temperature control schedule. If the temperature is not that is indicated by the temperature control schedule, a signal indicative of how to control the power in order to bring the temperature into agreement with the temperature control schedule is sent down line 56 to radiation control unit 32 of FIG. 2. When the current temperature is equal to the temperature as designated by the temperature versus time schedule system control is transferred by a signal from the temperature control unit 350 as indicated by line 352 to the central control unit 334. If the end point detection subsystem is desired system control is transferred by a signal from central control unit 334 as indicated by line 354 to block 356 which represents the end point detection routine. The current value of Q is determined by sending a signal along line 62 to prime mover 50 indicative of moving short 10 closer to the sample until the reflected powers is 30% of the forward power which is used to determine the value or Q. System control is transferred by a signal from block 356 as indicated by line 358 to the auto tune routine to bring the cavity hack into tune. Program control is transferred back from the auto tune routine 344 to the end point detector routine 356 as indicated by line 360 . The current Q value and the current T value are used to determine the current Z value which is compared to the expected Z value. If the current Z value is equal to the expected Z value system control is transferred by a signal from the end point detect routine of block 356 represented by line 358 to the central routine of block 334. If the current Z value is not equal to the expected Z value a signal indicative of increasing or decreasing the applied power to change the temperature ramp rate or to extend a temperature soak is sent through line 56 of FIG. 2 to radiation control unit 32. The input signals 360, 362, 364 which are indicative of forward power, reflected power, and temperature respectively are monitored $N_i$ times per second. The output signal 366 indicative of updating the display is outputted $N_d$ times per second. The autotune routine represented by block 344 is called $N_e$ times per second. The temperature control routine represented by block 350 is called $N_T$ times per second. The end point detect routine represented by block 356 is called $N_e$ times per second. The following inequality is generally applicable. $N_i > N_o > N_T > N_e$. $N_D$ is preferably one per second.

In summary, the autotune subsystem basically minimizes the reflected power by: determing the state of tune—using ratio of reflected to forward power, deciding if moving closer or away for minimum (local or global); determing the direction to move motors (defaulted initially)—based on above; determing the size of step to be made—smaller closer to tune; determing if a move is necessary (not necessary if tuned); determing if the axis should be changed (due to a local minimum); and moving the short or the antenna the desired distance in the desired direction. Alternatively, the short or antenna can be swept over a relatively large range and returned to the minimum position and then move the other axis in a similar manner or move it as described above, combinations of these two approaches may be applicable— eg. move motors stepwise until the ratio alpha starts to decrease and then go to a large swing of the motors. The size of the swing can decrease as the starting position of the movement is closer to tune.

In summary the temperature control subsystem: measures temperature, preferably surface temperature; determines the heating rate which is compared to an inputted temperature profile; and increases/decreases microwave power to obtain the appropriate heating rate or steady state temperature. The amount of change is determined by the system which controls the microwave generator preferably using an analog signal. The system stops when the heating cycle is complete (for example, by resetting flags).

In summary the end point detection subsystem: determines temperature; determines Q value, or similar for the cavity/workpiece; calculates Z factor or similar factor; compares Z factor or combination of Q and temperature with the desired profile; determines whether to end current segment (and move to next segment.) or end program execution; and determines whether to extend a segment if the Z or combination of temperature and Q are not as expected.

Although the invention has been described by reference to some embodiments it is not intended that the novel process and apparatus be limited thereby but that certain modifications are intended to be included as falling within the spirit and broad scope of the foregoing disclosure, the following claims and attached drawings.

We claim:

1. A system for controlling an application of radiation to a workpiece in a cavity comprising:

time tracking means for tracking current time;

means for receiving an applied power signal indicative of a magnitude of an applied intensity of said radiation;

means for receiving a reflected power signal indicative of a magnitude of a reflected intensity of said radiation;

means for receiving a temperature signal indicative of a magnitude of a temperature of said workpiece;

minimizing means coupled to said time tracking means, for causing α to be less than a predetermined value, α is a ratio of said magnitude of said reflected intensity over said magnitude of said applied intensity and to provide a signal corresponding to signal a current value of α signal corresponding to said current time;

said minimizing means being coupled to said time tracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

temperature control means coupled to said time tracking means, for producing an intensity signal indicative of said magnitude of said applied intensity of said radiation to control said temperature of said workpiece to be substantially equal to a predetermined temperature;

means for determining when said workpiece has achieved a final predetermined physical condition; said means for determining is coupled to said time tracking means; and means for producing an end signal to end operation of said system when said workpiece has achieved said final predetermined physical condition; said means for producing is coupled to said time tracking means.

2. The system of claim 1, further including, means for producing signals corresponding to said magnitude of said applied intensity, said magnitude of said reflected intensity and said temperature for visual display on a visual display means.

3. The system of claim 1, wherein said cavity further includes a short and an antenna and wherein said minimizing means produces signals to control a location of said short and said antenna in said cavity comprising:

means for receiving said current value of $\alpha$ signal means for generating a position signal indicative of an updated location of one member of the group consisting of said antenna and said short with respect to the position of said workpiece;

means for transmitting said position signal indicative of said updated location to said one member of the group consisting of said antenna and said short until said current value of $\alpha$ is at a local minimum;

when said local minimum is reached, said means for transmitting said position signal indicative of said updated location transmits said position signal indicative of said updated location to the other member of said group consisting of said short and said antenna; and when said current value of $\alpha$ is less than said predetermined value, said current value of $\alpha$ is minimized.

4. The system of claim 1, further including a schedule comprising a plurality of sets of numbers wherein each set has a temperature value and a time value each corresponding to said temperature of said workpiece and said current time, and wherein said temperature control means, which controls said temperature to be substantially in agreement with said schedule, comprises:

temperature hold determining means for producing a temperature hold signal when said temperature is to be held constant in accordance with said schedule and for producing a temperature test signal when said temperature is not to be held constant according to said schedule;

temperature test means for receiving said temperature test signal and for producing a temperature duration signal when said temperature is greater than a next hold temperature according to said schedule and for producing a heating rate determine signal when said temperature is not greater than said next hold temperature;

means for receiving said temperature duration signal and for producing a signal indicative of a temperature hold condition;

means for receiving said signal indicative of a temperature hold condition and for producing an initial time record signal;

means for receiving said initial time record signal and for receiving said temperature hold signal and for producing a temperature hold continue signal when said current time is in a region of said schedule indicative of holding said temperature constant and for producing a temperature hold discontinue signal when said current time is in a region of said schedule indicative of not holding said temperature constant;

means for receiving said temperature hold continue signal and for producing a temperature not correct signal when said temperature is different than indicated by said schedule for said current time and for producing a temperature desired signal when said temperature is not different than indicated by said schedule for said current time;

means for receiving said temperature not correct signal and for increasing said applied intensity when said temperature is lower than that indicated by said schedule and for decreasing said applied intensity when said temperature is greater than when indicated by said schedule, and for producing a temperature equal to desired signal and a heating rate determining signal;

means for receiving said heating rate determining signal and for determining a current heating rate and for producing a temperature rate compare signal;

means for receiving said temperature rate compare signal and for producing a temperature rate equal to an expected signal when said temperature rate is substantially equal to that indicated by said schedule for said current time and for producing a temperature rate not equal to expected signal when said temperature rate is not equal to that indicated by said schedule for said current time;

means for receiving said temperature rate not equal to expected signal and for producing a signal indicative of increasing said intensity when said current heating rate is less than indicated by said schedule for said current time and for producing a signal indicative of decreasing said intensity when said current heating rate is greater than indicated by said schedule for said current time and for producing a second temperature rate equal to expected signal when said current heating rate is substantially equal to said current heating rate indicated by said schedule for said current time; and means for determining when said current time is substantially equal to an end time of said schedule and for receiving said temperature equal to desired signal and for receiving said temperature not different than desired signal and for receiving said temperature hold discontinue signal and for producing a schedule end signal when said current time is not less than said end time and for producing a schedule not ended signal when said current time less than said end time.

5. The system of claim 1, wherein said means for determining when said workpiece has achieved a final predetermined physical condition comprises:

Q generating means for generating a signal representative of a current Q value;

means for executing said minimizing means to return said $\alpha$ value to a minimum;

means for determining from said current Q value and said temperature of said workpiece whether said workpiece has achieved said predetermined physical condition wherein said Q is the ratio of energy stored to energy lost in said cavity.

6. The system of claim 5, wherein said Q generating means generates a signal to place said $\alpha$ value in a nonminimized condition to determine said current Q value for said workpiece.

7. The system of claim 5, wherein said $\alpha$ value in said nonminimized condition is at a value of about 0.3.

8. A system for controlling an application of radiation to a workpiece having a position in a cavity comprising:

time tracking means for tracking current time;

means for receiving a forward power signal indicative of a magnitude of an applied intensity of said radiation;

means for receiving a reflected power signal indicative of a magnitude of a reflected intensity of said radiation;

means for receiving a temperature signal indicative of a magnitude of a temperature of said workpiece;

minimizing means for causing $\alpha$ to be less than a predetermined a value, wherein $\alpha$ is a ratio of said magnitude of said reflected intensity over said magnitude of said applied intensity and wherein a current value of $\alpha$ corresponding to said current time;

said minimizing means being coupled to said timetracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

means for producing an intensity signal indicative of an intensity of said radiation to control said temperature to be substantially equal to a predetermined temperature;

means for determining when said workpiece has achieved a final predetermined physical condition; and means for producing an end signal to end operation of said system when said workpiece has achieved said final predetermined physical condition;

said minimizing means which produces signals to control a location of a short and an antenna in said cavity comprises:

means for receiving a signal indicative of a current value of $\alpha$;

means for generating a position signal indicative of an updated location of one member of the group consisting of said antenna and said short with respect to a position of said workpiece, said one member being a selected member and the other member being an unselected member;

means for transmitting said position signal indicative of an updated location to said one member of the group consisting of said antenna and said short until said current value of $\alpha$ is at a local minimum;

when said local minimum is reached, said means for transmitting said position signal indicative of an updated location transmits said position signal indicative of an updated location to said unselected member of the group consisting of said short and said antenna;

when said current value of $\alpha$ is less than said predetermined $\alpha$ value, said current value of $\alpha$ is minimized;

a temperature control means, which controls a temperature to be substantially in agreement with a predetermined temperature versus time schedule, comprises:

temperature hold determining means for producing a temperature hold signal when said temperature is to be held constant in accordance with said schedule and for producing a temperature test signal when said temperature is not to be held constant according to said schedule;

temperature test means for receiving said temperature test signal and for producing a temperature duration signal when said temperature is greater than a next hold temperature according to said schedule and for producing a heating rate determine signal when said temperature is not greater than said next hold temperature;

means for receiving said temperature duration signal and for producing a signal indicative of a temperature hold condition;

means for receiving said signal indicative of a temperature hold condition and for producing an initial time record signal;

means for receiving said initial time record signal and for receiving said temperature hold signal and for producing a temperature hold continue signal when said current time is in a region of said schedule indicative of holding said temperature constant and for producing a temperature hold discontinue signal when said time is in a region of a schedule indicative of not holding said temperature constant;

means for receiving said temperature hold continue signal and for producing a temperature different than desired signal when said temperature is different than indicated by said schedule for said time and for producing a temperature not different than desired signal when said temperature is not different than desired;

means for receiving said temperature different than desired signal and for increasing said applied intensity when said temperature is lower than that indicated by said schedule indicative of not holding said temperature constant and for decreasing said intensity when said temperature is greater than when indicated by said schedule; indicative of not holding said temperature constant, and for producing a temperature equal to desired signal;

means for receiving said heating rate determining signal and for determining a current heating rate and for producing a temperature rate compare signal, means for receiving said temperature rate compare signal and for producing a temperature rate equal to expected signal when said temperature rate is substantially equal to that indicated by said schedule for said current time and for producing a temperature rate not equal to expected signal when said temperature rate is not equal to that indicated by said schedule for said current time;

means for receiving said temperature rate not equal to expected signal and for producing a signal indicative of increasing said intensity when said heating rate is less than indicated by said schedule for said current time and for producing a signal indicative of decreasing said intensity when said heating rate is greater than indicated by said schedule for said current time and for producing a second temperature rate equal to expected signal when said temperature rate is substantially equal to said rate indicated by said schedule for said time; and means for determining when said current time is substantially equal to an end time of said schedule and for receiving said temperature equal to desired signal and for receiving said temperature not different than desired signal and for receiving said temperature hold discontinue signal and for producing a schedule end signal when said current time is not less than said end time and for producing a schedule not ended signal when said current time less than said end time;

said means for determining when said workpiece has achieved a final predetermined physical condition comprises:

means for generating a signal to place said $\alpha$ value in a nonminimized condition to determine a current Q value for said workpiece;

means for executing said $\alpha$ minimizing means to return said $\alpha$ value to a minimum;

means for determining from said current Q value and said current temperature whether said workpiece has achieved said predetermined physical condition wherein said Q is the ratio of energy stored to energy lost in said cavity.

9. The system of claim 1, wherein said minimizing means comprises:

means for generating a signal to modify said cavity to vary said current value of $\alpha$;

means for determining in response to said varying said current value of $\alpha$ if said current value of $\alpha$ is increasing or decreasing; and means for generating a signal in response to said determination of whether said current value of $\alpha$ is increasing or decreasing, for modifying said cavity to minimize said current value of $\alpha$.

10. The system of claim 1, wherein said temperature control means comprises:

means for receiving specific temperature values of said temperature signal corresponding to specific time values of said current time;

means for producing a heating rate signal in response to determining a heating rate from said specific temperature value and said specific time values;

means for producing a comparison signal in response to determining a heating rate from said specific temperature values and said specific time values;

means for producing a comparison signal in response to comparing said heating rate signal with a predetermined temperature versus time schedule; and means for producing a signal to modify said forward power in response to said comparison signal.

11. The system of claim 1, wherein said means for determining when said workpiece has achieved a final predetermined physical condition comprises:

means for determining a current Q for said cavity; and means for comparing said current Q and said current temperature with a predetermined Q, temperature versus degrees of workpiece physical condition schedule.

12. A system for controlling an application or radiation to a workpiece in a cavity comprising:

time tracking means for tracking current time;

means for receiving an applied power signal indicative of the applied intensity of said radiation;

means for receiving a reflected power signal indicative of a magnitude of a reflected intensity of said radiation;

means for receiving a temperature signal indicative of a magnitude of a temperature of said workpiece;

a minimizing means coupled to said time tracking means for causing $\alpha$ to be less than a predetermined value, wherein $\alpha$ is a ratio of said magnitude of said reflected intensity over said magnitude of said applied intensity;

said minimizing means being coupled to said timetracking means, to said means for receiving said applied power signal indicative of said magnitude of said applied intensity, to said means for receiving said reflected power signal indicative of said magnitude of said reflected intensity and to said means for receiving said temperature signal indicative of said magnitude of said temperature of said workpiece;

temperature control means for producing an intensity signal indicative of a magnitude of an intensity of said radiation to control said temperature to be substantially equal to a predetermined temperature from a predetermined temperature versus time schedule;

means for determined when said workpiece has achieved a final predetermined physical condition, said means for determining is operatively connected to said time tracking means;

means for producing an end signal to end operation of said system when said workpiece has achieved said final predetermined physical condition, said means for producing is operatively connected to said time tracking means;

said minimizing means comprises:

means for generating a signal to modify said cavity to vary a value of $\alpha$;

means for determining in response to said varying said value of $\alpha$ if said value of $\alpha$ is increasing or decreasing; and means for generating a signal in response to a determination of whether said current value of $\alpha$ is increasing or decreasing, for modifying said cavity to minimize said current value of $\alpha$;

said temperature control means comprises:

means for receiving specific temperature values of said temperature signal corresponding to specific time values of said current time;

means for producing a heating rate signal in response to determining a heating rate from said specific temperature values and said specific time values;

means for producing a comparison signal in response to comparing said heating rate signal with said predetermined temperature versus time schedule; and means for producing a signal to modify said applied power signal indicative of the applied intensity in response to said comparison signal;

said means for determining when said workpiece has achieved a final predetermined physical condition comprises:

means for determining a current Q for said cavity wherein said current Q; and means for comparing said current Q and said current temperature with a predetermined Q, and temperature versus degree of workpiece physical condition schedule.

13. A method for controlling the application of radiation to a workpiece in a cavity comprising:

tracking current time;

measuring a forward radiation intensity applied to said workpiece at said current time;

measuring a reflected radiation intensity reflected from said workpiece at said current time;

minimizing $\alpha$ wherein $\alpha$ is a ratio of said magnitude of said reflected intensity over said magnitude of said applied intensity and wherein a current value of $\alpha$ corresponds to said current time;

measuring a temperature of said workpiece at said current time;

controlling a current temperature to be substantially equal to a predetermined temperature;

determining when said workpiece has achieved a final predetermined physical condition; and stopping said applied intensity when said workpiece has achieved said final predetermined physical condition.

14. The method of claim 13, further including producing and displaying on a visual display signals means corresponding to said radiation forward intensity, said reflected radiation intensity and said temperature.

15. The method of claim 13, wherein said step of minimizing a is achieved by controlling a location of an antenna and a short in said cavity by a method comprising:

determining said current value of $\alpha$;

moving to an updated location one member of the group consisting of said antenna and said short with respect to the position of said workpiece until a local minimum in said current value of $\alpha$ is achieved; and when said local minimum is achieved moving the other member of said group consisting of said short and said antenna until said current value of $\alpha$ is less than a predetermined value of $\alpha$.

16. The method of claim 13, wherein a current temperature is controlled to be substantially equal to a predetermined temperature indicated by a temperature versus time schedule, by a method comprising:

comparing said current temperature to said schedule:

determining if at said current time according to said schedule if said current temperature is to be held constant;

determining if at said current time according to said schedule if said current temperature is not to be held constant;

if said current temperature is to be held constant, determining when according to said schedule to change said temperature;

if said current temperature is not to be held constant, determining according to said schedule a current heating rate;

increasing applied incident intensity if said current temperature is less than that indicated by said schedule for said current time;

decreasing said incident intensity if said current temperature is greater than that indicated by said schedule for said current time; and determining when said current time is equal to an end time of said schedule.

17. The method of claim 13, wherein said step of determining when said workpiece has achieved a final predetermined physical condition comprises:

moving the position of one of member selected from the group consisting of said antenna and said short to place said $\alpha$ value at minimum condition;

determining at a nonminimum condition a current Q value for said workpiece;

returning said $\alpha$ value to a minimum;

determining from said current Q value and said current temperature whether said workpiece has achieved said predetermined physical condition.

18. The method of claim 16, wherein said $\alpha$ value in said nonminimum condition is at a value of about 0.3.

19. The method of claim 13, wherein said step of minimizing $\alpha$ comprises:

modifying said cavity to vary said current value of $\alpha$;

determining in response to said varying said current value of a if said current value of $\alpha$ is increasing or decreasing; and modifying said cavity to minimize said current value of $\alpha$.

20. The system of claim 13, wherein said step of controlling said current temperature comprises:

monitoring specific temperature values corresponding to specific time values;

determining a heating rate from said specific temperature values and said specific time values;

comparing said heating rate with a predetermined temperature versus time schedule; and modifying said forward radiation intensity in response to said comparing.

21. The method of claim 13, wherein said step of determining when said workpiece has achieved a final predetermined physical condition comprises:

determining a current Q for said cavity; and comparing said current Q and said current temperature with a predetermined Q, and temperature versus degree of workpiece physical condition schedule.

22. A method for controlling an application or radiation to a workpiece in a cavity comprising:

tracking current time;

measuring a forward radiation intensity applied to said workpiece at said current time;

measuring a reflected radiation intensity reflected from said workpiece at said current time;

minimizing $\alpha$ wherein $\alpha$ is a ratio of a magnitude of reflected radiation intensity over a magnitude of a said forward radiation intensity and wherein $\alpha$ has a current value corresponding to said current lime;

measuring a temperature of said workpiece at said current time;

controlling said temperature to be substantially equal to a predetermined temperature from a temperature versus time schedule;

determining when said workpiece has achieved a final predetermined physical condition;

stopping said forward radiation intensity when said workpiece has achieved said final predetermined physical condition;

said step of minimizing $\alpha$ comprises:

modifying said cavity to vary said current value of $\alpha$;

determining in response to said varying said current value of $\alpha$ if said current value of $\alpha$ is increasing or decreasing; and modifying said cavity to minimize said current value of $\alpha$;

said step of controlling said temperature comprises:

monitoring specific temperature values corresponding to specific time values;

determining a heating rate from said specific temperature values and said specific time values;

comparing said heating rate with said predetermined temperature versus time schedule; and modifying said forward radiation intensity in response to said step of comparing said heating;

said step of determining when said workpiece has achieved a final predetermined physical condition comprises:

determining a current Q value for said cavity; and comparing said current Q and said current temperature with a predetermined Q, and temperature versus degree of workpiece physical condition schedule.

* * * * *